(12) United States Patent
Kasamatsu et al.

(10) Patent No.: US 9,392,944 B2
(45) Date of Patent: *Jul. 19, 2016

(54) LASER SOURCE UNIT, CONTROL METHOD THEREOF, PHOTOACOUSTIC IMAGE GENERATION APPARATUS AND PHOTOACOUSTIC IMAGE GENERATION METHOD

(71) Applicant: FUJIFILM Corporation, Tokyo (JP)

(72) Inventors: Tadashi Kasamatsu, Kanagawa (JP); Kaku Irisawa, Kanagawa (JP); Kazuhiro Hirota, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 46 days.

This patent is subject to a terminal disclaimer.

(21) Appl. No.: 14/167,739

(22) Filed: Jan. 29, 2014

(65) Prior Publication Data

US 2014/0148680 A1  May 29, 2014

Related U.S. Application Data

(63) Continuation of application No. PCT/JP2012/068910, filed on Jul. 26, 2012.

(30) Foreign Application Priority Data

Jul. 29, 2011 (JP) ................................. 2011-166979
Jul. 19, 2012 (JP) ................................. 2012-160425

(51) Int. Cl.
*A61B 5/00* (2006.01)
*H01S 3/106* (2006.01)
(Continued)

(52) U.S. Cl.
CPC ........... *A61B 5/0095* (2013.01); *A61B 5/14542* (2013.01); *G01N 21/1702* (2013.01);
(Continued)

(58) Field of Classification Search
CPC ............... A61B 5/0075; A61B 5/0095; A61B 5/14542; A61B 5/14551; A61B 5/7257; G01N 21/1702; G01N 2291/02466; G01N 29/2418; H01S 3/061; H01S 3/08; H01S 3/092; H01S 3/1062; H01S 3/11
See application file for complete search history.

(56) References Cited

U.S. PATENT DOCUMENTS 3,609,586 A    9/1971  Danielmeyer
4,272,733 A *  6/1981  Walling et al. .................. 372/20
(Continued)

FOREIGN PATENT DOCUMENTS

CN    102095685 A    6/2011
JP    2000-105464 A  4/2000
(Continued)

OTHER PUBLICATIONS

Extended European Search Report, dated May 15, 2015, for European Application No. 12820101.9.
(Continued)

*Primary Examiner* — Jonathan Cwern
(74) *Attorney, Agent, or Firm* — Birch, Stewart, Kolasch & Birch, LLP

(57) ABSTRACT

A pulse laser beam is emitted in a desired wavelength sequence using a laser light source unit. A Q switch and a birefringent filter are inserted into an optical resonator including a pair of mirrors and facing each other with a laser rod interposed therebetween. The birefringent filter changes an oscillation wavelength of the optical resonator in association with rotational displacement. The rotation control unit rotates the birefringent filter at a predetermined rotation speed depending on the number of wavelengths included in the wavelength sequence of the pulse laser beam to be emitted. An emission control unit irradiates the laser rod with excitation light, and then turns on the Q switch at a timing when a rotational-displacement-position of the birefringent filter is set to a position corresponding to the wavelength of the pulse laser beam to be emitted, to cause the pulse laser beam to be emitted.

13 Claims, 13 Drawing Sheets

(51) Int. Cl.
  *H01S 3/11*   (2006.01)
  *G01N 29/24*  (2006.01)
  *A61B 5/145*  (2006.01)
  *G01N 21/17*  (2006.01)
  *H01S 3/08*   (2006.01)
  *A61B 5/1455* (2006.01)
  *H01S 3/092*  (2006.01)
  *H01S 3/06*   (2006.01)

(52) U.S. Cl.
  CPC .............. *G01N29/2418* (2013.01); *H01S 3/08* (2013.01); *H01S 3/1062* (2013.01); *H01S 3/11* (2013.01); *A61B 5/0075* (2013.01); *A61B 5/14551* (2013.01); *A61B 5/7257* (2013.01); *G01N 2291/02466* (2013.01); *H01S 3/061* (2013.01); *H01S 3/092* (2013.01)

(56) References Cited

U.S. PATENT DOCUMENTS

| | | | |
|---|---|---|---|
| 4,809,283 A * | 2/1989 | Harter | 372/41 |
| 4,891,738 A | 1/1990 | Richardson et al. | |
| 5,107,509 A | 4/1992 | Esterowitz et al. | |
| 5,175,736 A * | 12/1992 | Woodward et al. | 372/20 |
| 6,979,292 B2 | 12/2005 | Kanayama et al. | |
| 7,777,881 B2 | 8/2010 | Yamazoe | |
| 2003/0072333 A1 * | 4/2003 | Jacobowitz et al. | 372/20 |
| 2003/0118060 A1 * | 6/2003 | Spuehler et al. | 372/18 |
| 2005/0187471 A1 * | 8/2005 | Kanayama et al. | 600/437 |
| 2014/0148681 A1 * | 5/2014 | Hirota et al. | 600/407 |
| 2014/0148682 A1 * | 5/2014 | Hirota et al. | 600/407 |

FOREIGN PATENT DOCUMENTS

| | | |
|---|---|---|
| JP | 2006-324601 A | 11/2006 |
| JP | 2007-81065 A | 3/2007 |
| JP | 2010-046215 A | 3/2010 |
| WO | WO 2011/022547 A2 | 2/2011 |

OTHER PUBLICATIONS

A High-Speed Photoacoustic Tomography System based on a Commercial Ultrasound and a Custom Transducer Array, Xueding Wang, Jonathan Cannata, Derek DeBusschere, Changhong Hu, J. Brian Fowlkes, and Paul Carson, Proc. SPIE vol. 7564, 756424 (Feb. 23, 2010).

International Search Report, mailed Jul. 26, 2012, issued in PCT/JP2012/068910.

Written Opinion of the International Search Authority, mailed Jul. 26, 2012, issued in PCT/JP2012/068910.

Notice of Reasons for Allowance dated Jul. 3, 2015 for Chinese Application No. 201280037135.4.

* cited by examiner

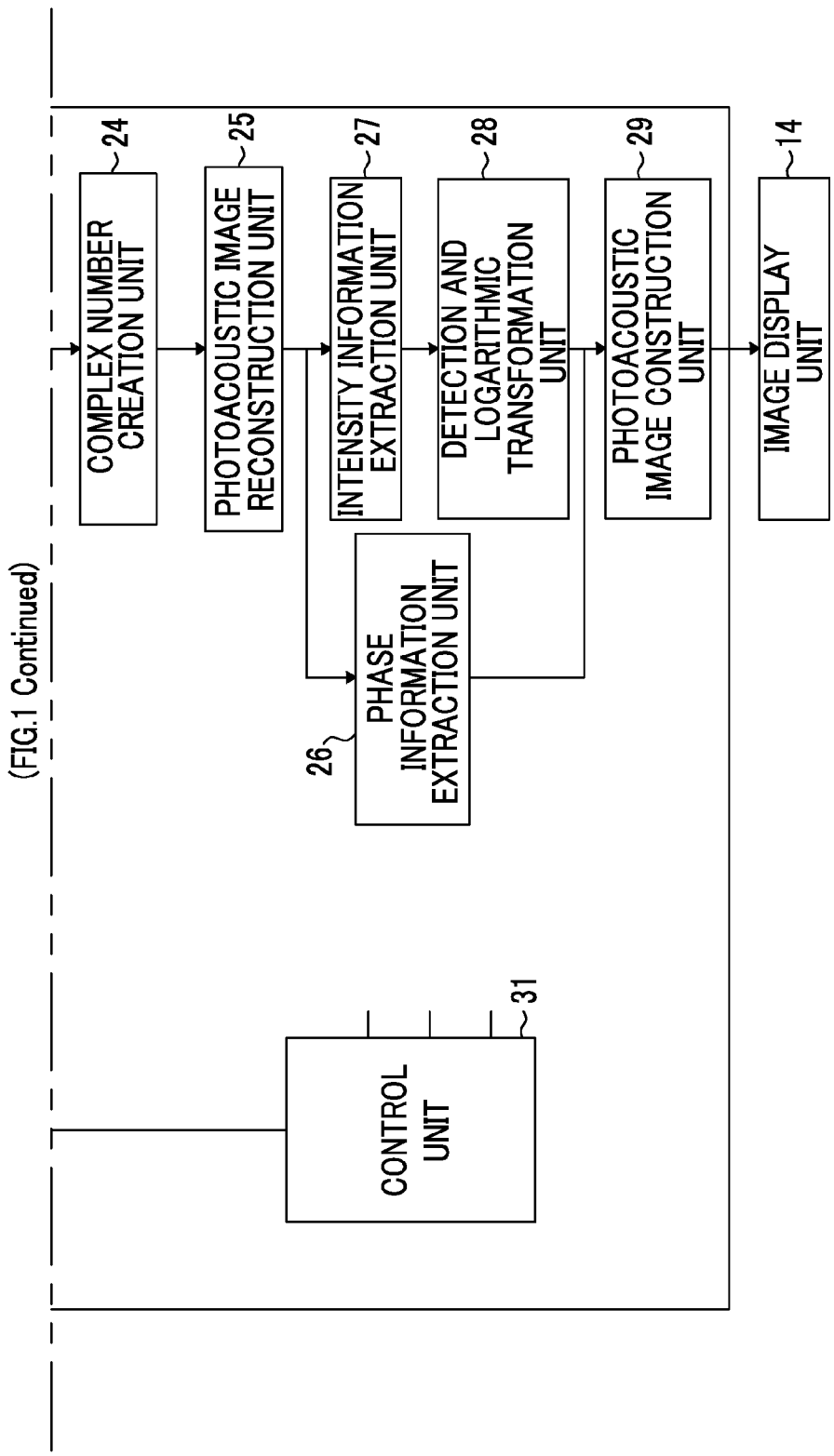

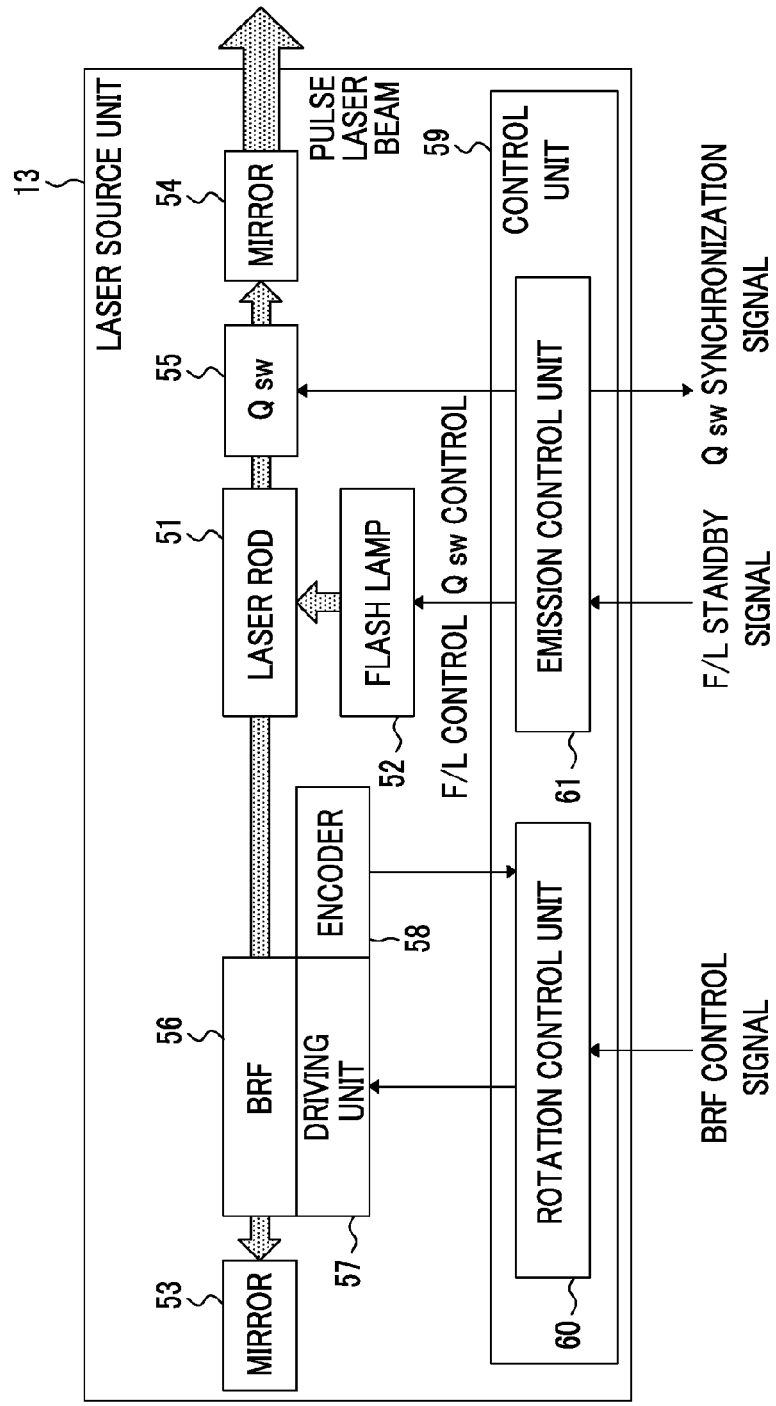

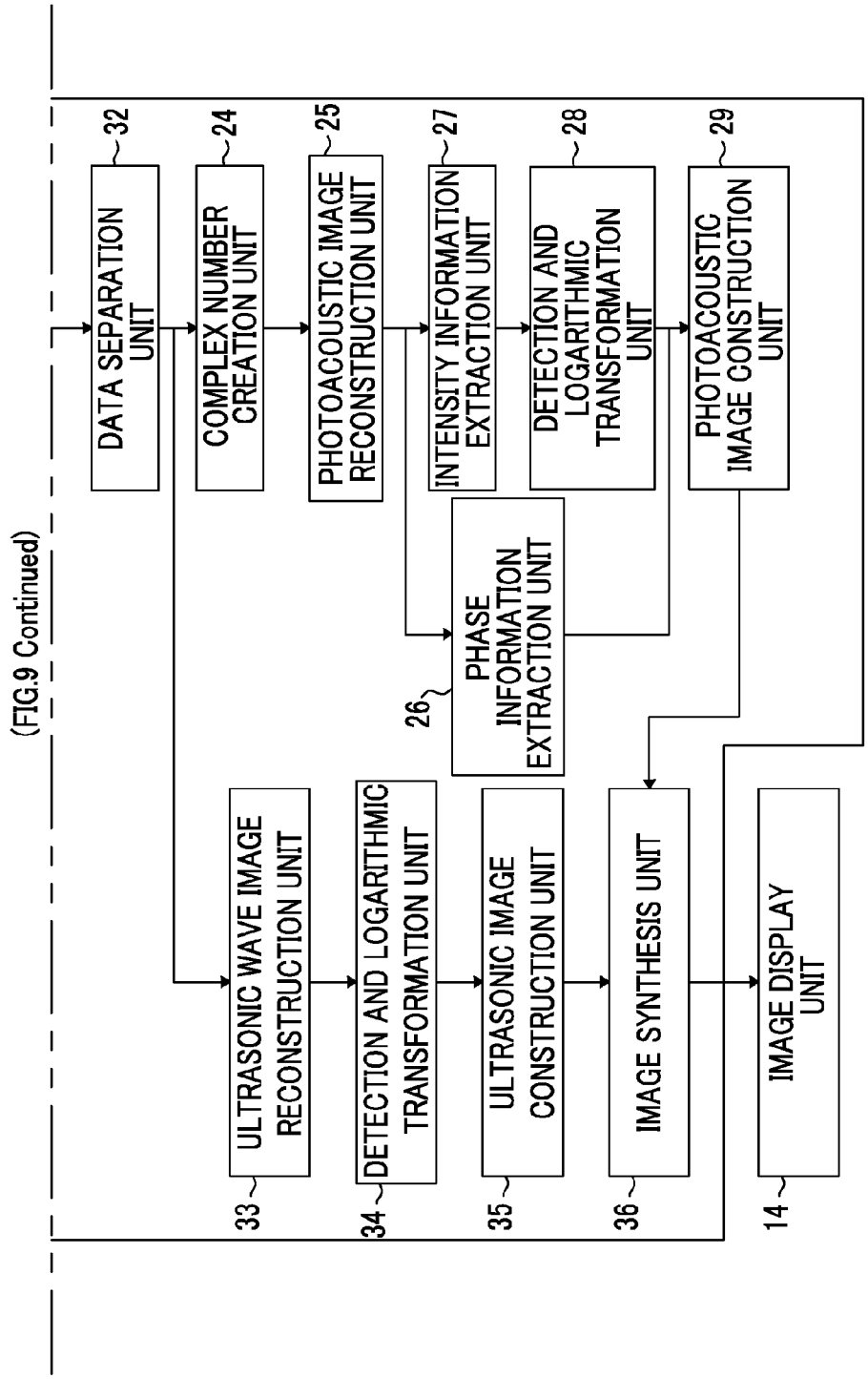

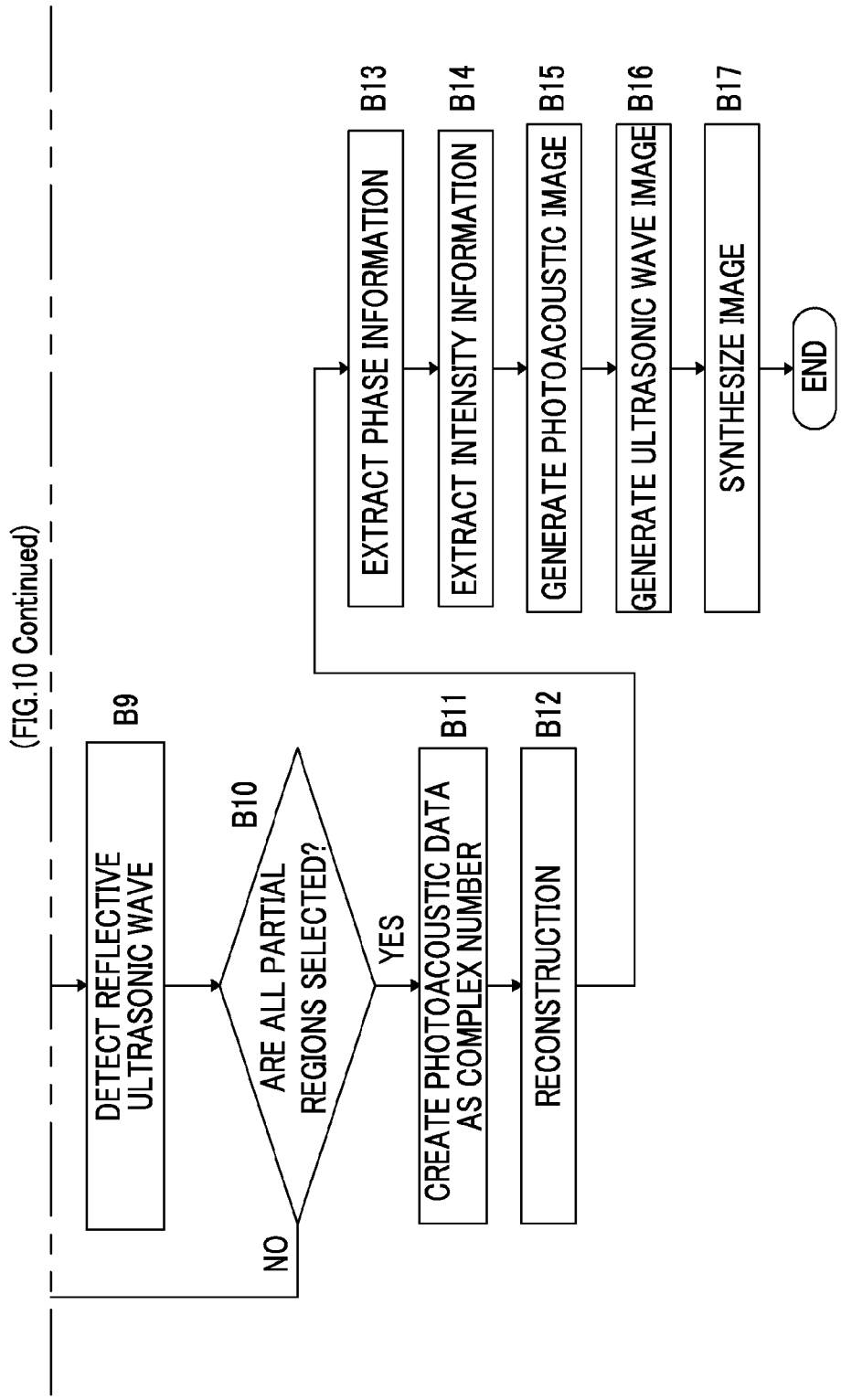

LASER SOURCE UNIT, CONTROL METHOD THEREOF, PHOTOACOUSTIC IMAGE GENERATION APPARATUS AND PHOTOACOUSTIC IMAGE GENERATION METHOD

CROSS REFERENCE TO RELATED APPLICATIONS

This application is a continuation of PCT International Application No. PCT/JP2012/068910 filed on Jul. 26, 2012, which claims priority under 35 U.S.C 119(a) to Application No. 2011-166979 filed on Jul. 29, 2011 and Application No. 2012-160425 filed on Jul. 19, 2012 both filed in Japan, all of which are hereby expressly incorporated by reference into the present application.

BACKGROUND OF THE INVENTION

1. Field of the Invention

The present invention relates to a laser light source unit and a control method thereof, and more particularly, to a laser light source unit capable of switching and emitting a laser beam having a plurality of wavelengths, and a control method thereof.

In addition, the present invention relates to a photoacoustic image generation apparatus and a photoacoustic image generation method, and more particularly, to a photoacoustic image generation apparatus which irradiates a test object with a laser beam having a plurality of wavelengths to detect a photoacoustic signal and generates a photoacoustic image on the basis of the detected photoacoustic signal, and a photoacoustic image generation method.

2. Description of the Related Art

Hitherto, for example, as disclosed in JP2005-21380A and A High-Speed Photoacoustic Tomography System based on a Commercial Ultrasound and a Custom Transducer Array, Xueding Wang, Jonathan Cannata, Derek DeBusschere, Changhong Hu, J. Brian Fowlkes, and Paul Carson, Proc. SPIE Vol. 7564, 756424 (Feb. 23, 2010), a photoacoustic image forming apparatus that forms an image of the inside of a living body using a photoacoustic effect has been known. In the photoacoustic image forming apparatus, a living body is irradiated with pulsed light such as a pulse laser beam. Body tissues absorbing energy of the pulsed light expand in volume inside the living body irradiated with the pulsed light, and thus acoustic waves are generated. It is possible to detect the acoustic waves using an ultrasonic probe or the like, and to form a visible image of the inside of the living body on the basis of the detected signal (photoacoustic signal). In a photoacoustic image forming method, acoustic waves are generated in a specific light absorber, and thus it is possible to form an image of specific tissues in the living body, for example, blood vessels.

Incidentally, many of body tissues have an optical absorption property varying depending on a wavelength of light, and generally, the optical absorption property is unique for each tissue. For example, FIG. 11 illustrates molecular absorption coefficients of oxygenated hemoglobin (hemoglobin combined with oxygen: oxy-Hb) which is contained in a large amount in an artery of a human and deoxygenated hemoglobin (hemoglobin not combined with oxygen: deoxy-Hb) which is contained in a large amount in a vein, according to light wavelengths. An optical absorption property of an artery corresponds to that of oxygenated hemoglobin, and an optical absorption property of a vein corresponds to that of deoxygenated hemoglobin. There is known a photoacoustic image forming method of irradiating blood vessel parts with a light beam having two different types of wavelengths and of distinctively forming images of an artery and a vein (for example, see JP2010-046215A), using a difference in light absorptivity according to the wavelengths.

Herein, with regard to a variable wavelength laser, JP2009-231483A discloses that a laser beam having a desired wavelength is obtained by disposing an etalon or a birefringent filter as a wavelength selection element within an optical resonator and adjusting the rotation angle thereof. In addition, JP2000-105464A discloses that an etalon as wavelength selection means is disposed within an optical resonator and that the etalon is scanned at a constant speed. JP2000-105464A discloses that laser oscillation is performed only when a transmission wavelength of the etalon is consistent with longitudinal mode oscillation of a laser beam and that the oscillation of the laser beam is performed in a pulsed manner when a scanning speed of the etalon is increased.

SUMMARY OF THE INVENTION

In JP2009-231483A, in order to switch and emit a laser beam having a plurality of wavelengths, it is necessary to adjust a rotation angle of the etalon or the birefringent filter at every laser emission. In photoacoustic imaging, for example, it is considered that when a test object is irradiated with pulse laser beams having a first wavelength and a second wavelength, the wavelength selection element is adjusted to irradiate the test object with the laser beam having the first wavelength, the detection of all photoacoustic signals of the laser beam having the first wavelength is terminated, and then the wavelength selection element is adjusted so as to emit the laser beam having the second wavelength, and the test object is irradiated with the laser beam having the second wavelength. In the photoacoustic imaging, an object having a movement such as a human is often used. Therefore, when an object moves during switching from the first wavelength to the second wavelength, mismatching may occur between a photoacoustic signal at the time of irradiation with the laser beam having the first wavelength and a photoacoustic signal at the time of irradiation with the laser beam having the second wavelength.

In the photoacoustic imaging, in terms of the prevention of the above-mentioned mismatching, for example, it is considered that the irradiation with a laser beam may be performed by switching the first wavelength and the second wavelength for each pulse. In other words, for example, it is considered that the irradiation with the laser beam may be repeatedly performed in a predetermined wavelength sequence including the first wavelength and the second wavelength in this order. JP2000-105464A discloses a laser device that changes a wavelength of a laser beam with which the irradiation is performed for each pulse. However, in JP2000-105464A, since a laser is oscillated only when the transmission wavelength of the etalon is consistent with the longitudinal mode oscillation of the laser beam, a laser beam having only a specific wavelength sequence can be obtained, and a laser beam having any wavelength sequence cannot be obtained.

The invention is contrived in view of such situations, and an object thereof is to provide a laser light source unit capable of emitting a pulse laser beam in a desired wavelength sequence, and a control method thereof. In addition, the invention provides a photoacoustic image generation apparatus including such a laser light source unit, and a photoacoustic image generation method using a method of controlling the laser light source unit.

In order to achieve the above-described object, the invention provides a laser light source unit that sequentially emits a plurality of pulse laser beams in a predetermined wavelength sequence including at least two different wavelengths, the laser light source unit including: a laser rod; an excitation light source that irradiates the laser rod with excitation light; an optical resonator including a pair of mirrors facing each other with the laser rod interposed therebetween; a Q switch which is inserted into the optical resonator; a birefringent filter which is inserted into the optical resonator and changes an oscillation wavelength of the optical resonator in association with rotational displacement of the birefringent filter; a rotation control unit that rotates the birefringent filter at a predetermined rotation speed depending on the number of wavelengths included in the wavelength sequence; and an emission control unit that irradiates the laser rod with excitation light from the excitation light source and then turns on the Q switch, at a timing when a rotational displacement position of the birefringent filter is set to a position corresponding to the wavelength of the pulse laser beam to be emitted, to cause the pulse laser beam to be emitted.

In the invention, the predetermined rotation speed may be determined on the basis of change characteristics of an oscillation wavelength for the rotational displacement position in the birefringent filter, the number of wavelengths included in the wavelength sequence, and the number of times of emission of the pulse laser beam per unit time.

When the number of times of a free spectral range repeated during one rotation is set to k[times/rotation], the number of wavelengths included in the wavelength sequence is set to n[pieces], and the number of times of emission of the pulse laser beam per unit time is set to m[times/second], the predetermined rotation speed of the birefringent filter may be determined as a value calculated by a relation of $v=m/(k\times n)$[rotations/second].

In the invention, the rotation control unit may continuously rotate the birefringent filter in a predetermined direction at the predetermined rotation speed.

The laser light source unit of the invention may further include driving unit that rotates the birefringent filter, and rotational displacement detection unit that detects the rotational displacement of the birefringent filter. The rotation control unit may control the driving unit so that the amount of rotational displacement of the birefringent filter detected by the rotational displacement detection unit for a predetermined period of time is set to an amount depending on the predetermined rotation speed.

Moreover, the birefringent filter may be rotated by a stepping motor, and the rotation control unit may control a pulse interval of a pulse signal supplied to the stepping motor so that the birefringent filter is rotated at the predetermined rotation speed.

The invention also provides a photoacoustic image generation apparatus including: a laser light source unit that sequentially emits a plurality of pulse laser beams in a predetermined wavelength sequence including at least two different wavelengths; detection unit that detects a photoacoustic signal generated within an object when the object is irradiated with the pulse laser beam having each wavelength included in the predetermined wavelength sequence, and generates pieces of photoacoustic data corresponding to the respective wavelengths; intensity ratio extraction unit that extracts a magnitude relation between relative signal intensities of the pieces of photoacoustic data corresponding to the respective wavelengths; and photoacoustic image construction unit that generates a photoacoustic image on the basis of the extracted magnitude relation. The laser light source unit includes a laser rod; an excitation light source that irradiates the laser rod with excitation light; an optical resonator including a pair of mirrors facing each other with the laser rod interposed therebetween; a Q switch which is inserted into the optical resonator; a birefringent filter which is inserted into the optical resonator and changes an oscillation wavelength of the optical resonator in association with rotational displacement of the birefringent filter; a rotation control unit that rotates the birefringent filter at a predetermined rotation speed depending on the number of wavelengths included in the wavelength sequence; and an emission control unit that irradiates the laser rod with excitation light from the excitation light source and then turns on the Q switch, at a timing when a rotational displacement position of the birefringent filter is set to a position corresponding to the wavelength of the pulse laser beam to be emitted, to cause the pulse laser beam to be emitted.

The photoacoustic image generation apparatus may further include intensity information extraction unit that generates intensity information indicating signal intensity on the basis of the pieces of photoacoustic data corresponding to the respective wavelengths. The photoacoustic image construction unit may determine a gradation value of each pixel of the photoacoustic image on the basis of the intensity information, and may determine a display color of each pixel on the basis of the extracted magnitude relation.

The predetermined wavelength sequence may include a first wavelength and a second wavelength. The photoacoustic image generation apparatus may further include: complex number creation unit that generates complex number data in which one of first photoacoustic data corresponding to a photoacoustic signal, detected when irradiation with the pulse laser beam having the first wavelength is performed, and second photoacoustic data corresponding to a photoacoustic signal, detected when irradiation with the pulse laser beam having the second wavelength is performed, is set to a real part and the other one is set to an imaginary part; and photoacoustic image reconstruction unit that generates a reconstructed image from the complex number data using a Fourier transform method. The intensity ratio extraction unit may extract the magnitude relation from the reconstructed image, and the intensity information extraction unit may extract the intensity information from the reconstructed image.

The detection unit may further detect reflected acoustic waves with respect to acoustic waves transmitted to the object to generate reflected acoustic wave data, and the photoacoustic image generation apparatus may further include acoustic wave image generation unit that generates an acoustic wave image on the basis of the reflected acoustic wave data.

Furthermore, the invention provides a method of controlling a laser light source unit that sequentially emits a plurality of pulse laser beams, using the laser source unit, in a predetermined wavelength sequence including at least two different wavelengths, the method including: a step of rotating, at a predetermined rotation speed, a birefringent filter which is inserted into an optical resonator including a pair of mirrors facing each other with a laser rod interposed therebetween and changes an oscillation wavelength of the optical resonator in association with rotational displacement of the birefringent filter; and a step of irradiating the laser rod with excitation light, and after the irradiation with the excitation light, turning on a Q switch inserted into the optical resonator, at a timing when a rotational displacement position of the birefringent filter is set to a position corresponding to the wavelength of the pulse laser beam to be emitted, to cause the pulse laser beam to be emitted.

The invention also provides photoacoustic image generation method including: a step, which is a step of sequentially emitting a plurality of pulse laser beams, using the photoacoustic image generation apparatus, in a predetermined wavelength sequence including at least two different wavelengths, of irradiating a laser rod with excitation light while rotating, at a predetermined rotation speed, a birefringent filter which is inserted into an optical resonator including a pair of mirrors facing each other with the laser rod interposed therebetween and changes an oscillation wavelength of the optical resonator in association with rotational displacement of the birefringent filter, and after the irradiation with the excitation light, turning on a Q switch inserted into the optical resonator, at a timing when a rotational displacement position of the birefringent filter is set to a position corresponding to the wavelength of the pulse laser beam to be emitted, to cause the pulse laser beam to be emitted; a step of detecting a photoacoustic signal generated within an object when the object is irradiated with the pulse laser beam having each wavelength included in the predetermined wavelength sequence, and generating pieces of photoacoustic data corresponding to the respective wavelengths; a step of extracting a magnitude relation between relative signal intensities of the pieces of photoacoustic data corresponding to the respective wavelengths; and a step of generating a photoacoustic image on the basis of the extracted magnitude relation.

In a photoacoustic image generation apparatus and an acoustic wave unit of the invention, a birefringent filter which is inserted into an optical resonator and changes an oscillation wavelength in association with rotational displacement of the birefringent filter is rotated at a rotation speed depending on the number of wavelength sequences of a pulse laser beam to be emitted from a laser light source unit, and a Q switch inserted into the optical resonator is turned on at a timing when a rotational displacement position of the birefringent filter is set to a position corresponding to a wavelength of the pulse laser beam to be emitted. As the rotation speed of the birefringent filter increases, the speed of the wavelength switching can be increased. On the contrary, as the rotation speed thereof decreases, the number of selectable oscillation wavelengths can be increased. In the invention, the rotation speed of the birefringent filter is controlled depending on the number of wavelengths included in a wavelength sequence. Based on such a configuration, the wavelengths of the pulse laser beam to be emitted from the laser light source unit can be controlled to have any wavelength sequence by the acoustic wave unit.

BRIEF DESCRIPTION OF THE DRAWINGS

FIG. 2 is a block diagram illustrating a configuration of a laser light source unit according to the first embodiment.

DESCRIPTION OF THE PREFERRED EMBODIMENTS

Figure 1:
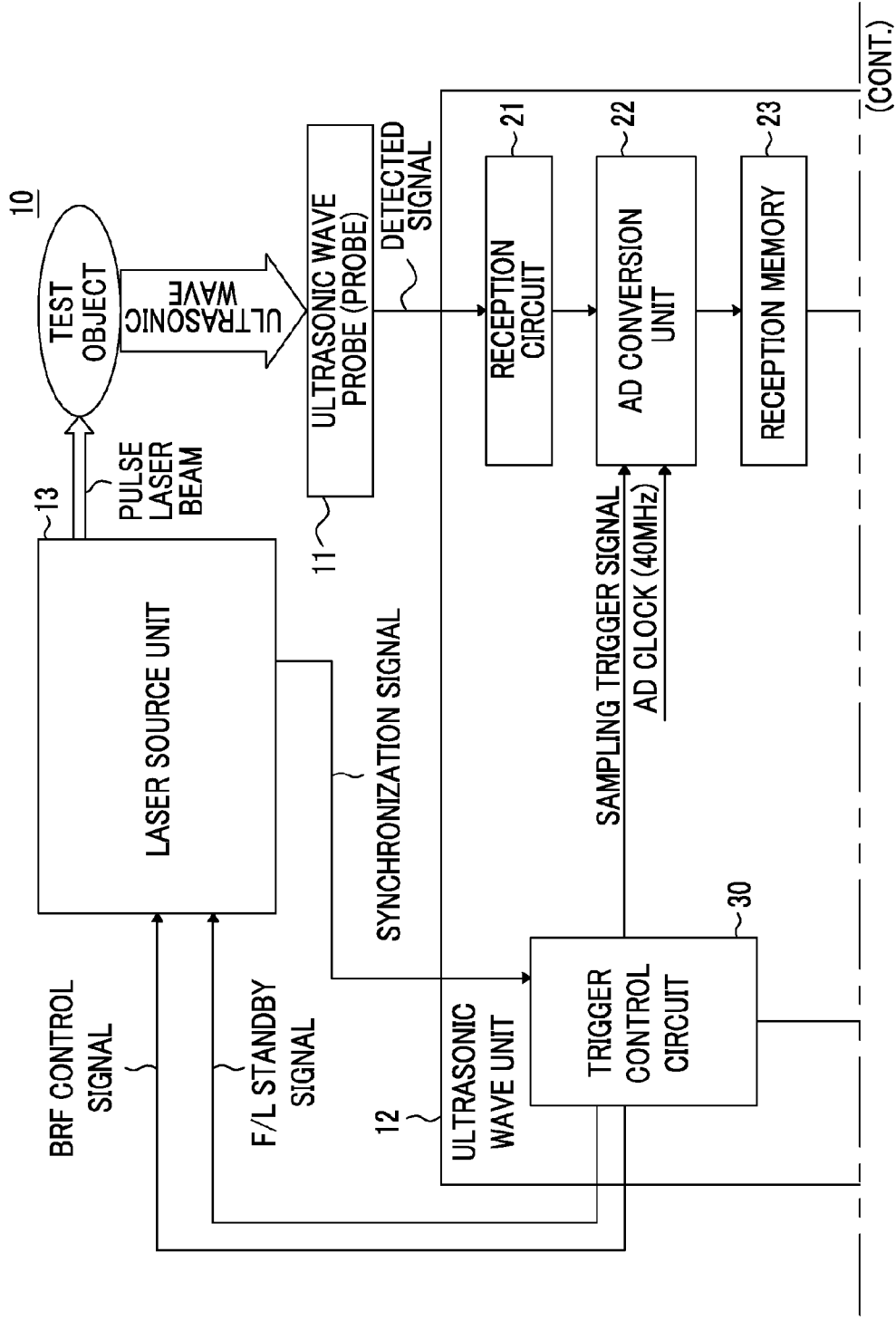
FIG. 1 is a block diagram of a photoacoustic image generation apparatus according to a first embodiment of the invention.

Hereinafter, embodiments of the invention will be described in detail with reference to the accompanying drawings. Meanwhile, in examples of the invention, ultrasonic waves are used as acoustic waves, but the acoustic waves may be acoustic waves having an audible frequency by selecting an appropriate frequency according to an object to be tested or measurement conditions. FIG. 1 illustrates a photoacoustic image generation apparatus according to a first embodiment of the invention. A photoacoustic image generation apparatus 10 includes an ultrasonic wave probe (probe) 11, an ultrasonic wave unit 12, and a laser light source unit 13. The laser light source unit 13 emits a pulse laser beam with which a test object is to be irradiated. The laser light source unit 13 emits a plurality of pulse laser beams in a predetermined wavelength sequence including at least two different wavelengths. Hereinafter, a description will be mainly given on the assumption that the wavelength sequence includes a first wavelength and a second wavelength in this order and the laser light source unit 13 emits a pulse laser beam having the first wavelength and a pulse laser beam having the second wavelength in this order.

Figure 11:
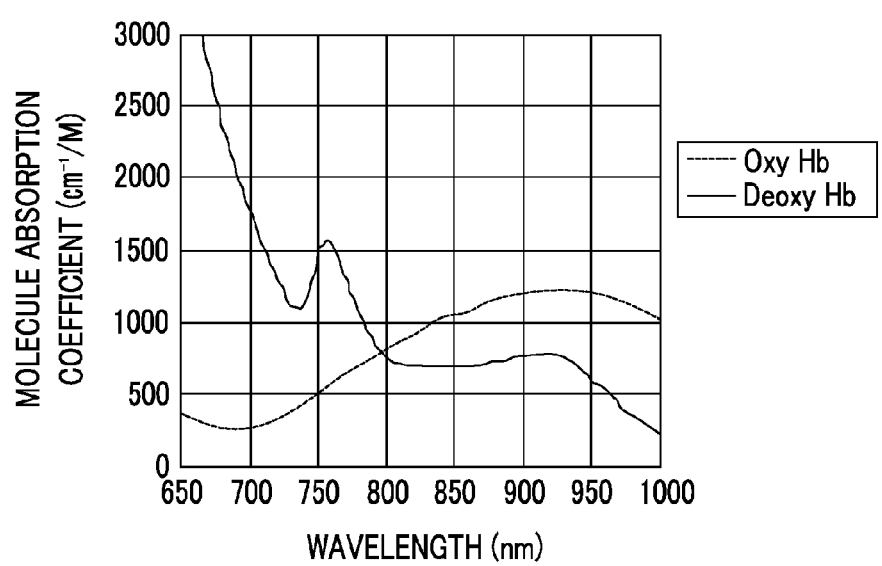
FIG. 11 is a graph illustrating molecular absorption coefficients of oxygenated hemoglobin and deoxygenated hemoglobin depending on light wavelengths.

For example, a wavelength of approximately 750 nm is considered as the first wavelength (center wavelength), and a wavelength of approximately 800 nm is considered as the second wavelength. First, referring to FIG. 11 described above, a molecular absorption coefficient of oxygenated hemoglobin (hemoglobin combined with oxygen: oxy-Hb) which is contained in a large amount in an artery of a human at a wavelength of 750 nm is lower than a molecular absorption coefficient of that at a wavelength of 800 nm. On the other hand, a molecular absorption coefficient of deoxygenated hemoglobin (hemoglobin not combined with oxygen: deoxy-Hb) which is contained in a large amount in a vein at a wavelength of 750 nm is higher than a molecular absorption coefficient of that at a wavelength of 800 nm. It is possible to discriminate between a photoacoustic signal from the artery and a photoacoustic signal from the vein by examining whether a photoacoustic signal obtained at the wavelength of 750 nm is relatively larger or smaller than a photoacoustic signal obtained at the wavelength of 800 nm, using such a property.

The pulse laser beam emitted from the laser light source unit 13 is guided to a probe 11 using light guiding means such as an optical fiber, and is irradiated toward a test object from the probe 11. An irradiation position of the pulse laser beam is not particularly limited, and the pulse laser beam may be irradiated from any place other than the probe 11. Ultrasonic waves (acoustic waves) are generated within the test object by a light absorber absorbing energy of the irradiated pulse laser beam. The probe 11 includes an ultrasonic wave detector. The probe 11 includes, for example, a plurality of ultrasonic wave detector elements (ultrasonic wave vibrators) which are arranged one-dimensionally, and the acoustic waves (photoacoustic signal) from the inside of the test object are detected by the ultrasonic wave vibrators that are arranged one-dimensionally.

The ultrasonic wave unit 12 includes a reception circuit 21, AD conversion unit 22, a reception memory 23, complex number creation unit 24, photoacoustic image reconstruction unit 25, phase information extraction unit 26, intensity information extraction unit 27, detection and logarithmic transformation unit 28, photoacoustic image construction unit 29, a trigger control circuit 30, and control unit 31. The reception circuit 21 receives a photoacoustic signal detected by the probe 11. The AD conversion unit 22, which is detection unit, samples the photoacoustic signal received by the reception circuit 21 and generates photoacoustic data which is digital data. The AD conversion unit 22 samples the photoacoustic signal with a predetermined sampling period in synchronization with an AD clock signal.

The AD conversion unit 22 stores photoacoustic data in the reception memory 23. The AD conversion unit 22 stores, in the reception memory 23, photoacoustic data corresponding to the respective wavelengths of the pulse laser beam emitted from the laser light source unit 13. In other words, the AD conversion unit 22 stores, in the reception memory 23, first photoacoustic data converted from a photoacoustic signal detected by the probe 11 when a test object is irradiated with a pulse laser beam having a first wavelength and second photoacoustic data converted from a photoacoustic signal detected by the probe 11 when the test object is irradiated with a second pulse laser beam.

The complex number creation unit 24 reads out the first photoacoustic data and the second photoacoustic data from the reception memory 23, and generates complex number data in which any one of the first photoacoustic data and the second photoacoustic data is set to a real part and the other one is set to an imaginary part. Hereinafter, a description will be given on the assumption that the complex number creation unit 24 generates the complex number data in which the first photoacoustic data is set to a real part and the second photoacoustic data is set to an imaginary part.

The photoacoustic image reconstruction unit 25 inputs the complex number data from the complex number creation unit 24. The photoacoustic image reconstruction unit 25 performs image reconstruction from the input complex number data using a Fourier transform method (FTA method). A well-known method of the related art which is disclosed in, for example, a document "Photoacoustic Image Reconstruction-A Quantitative Analysis" Jonathan I. Sperl et al. SPIE-OSA, Vol. 6631 663103 can be applied to the image reconstruction using the Fourier transform method. The photoacoustic image reconstruction unit 25 inputs data indicating the reconstructed image through Fourier transformation to the phase information extraction unit 26 and the intensity information extraction unit 27.

The phase information extraction unit 26, which is intensity ratio extraction unit, extracts a magnitude relation between relative signal intensities of pieces of photoacoustic data corresponding to the respective wavelengths. In this embodiment, the phase information extraction unit 26 sets the reconstructed image reconstructed by the photoacoustic image reconstruction unit 25 to input data. In addition, the phase information extraction unit generates, when the real part and the imaginary part are compared with each other, phase information indicating how relatively large either of the two parts is. For example, when the complex number data is expressed by X+iY, the phase information extraction unit 26 generates the relation of $\theta=\tan^{-1}(Y/X)$ as phase information. Meanwhile, when the relation of X=0 is satisfied, the relation of $\theta=90°$ is established. When first photoacoustic data (X) constituting the real part is equal to second photoacoustic data (Y) constituting the imaginary part, the phase information satisfies the relation of $\theta=45°$. As the first photoacoustic data becomes relatively larger, the phase information becomes closer to the relation of $\theta=0°$. As the second photoacoustic data becomes larger, the phase information becomes closer to the relation of $\theta=90°$.

The intensity information extraction unit 27 generates intensity information indicating signal intensity on the basis of the pieces of photoacoustic data corresponding to the respective wavelengths. In this embodiment, the intensity information extraction unit 27 sets the reconstructed image reconstructed by the photoacoustic image reconstruction unit 25 to input data, and generates the intensity information from the input data which is complex number data. For example, when the complex number data is expressed by X+iY, the intensity information extraction unit 27 extracts $(X^2+Y^2)^{1/2}$ as intensity information. The detection and logarithmic transformation unit 28 generates an envelope of data indicating the intensity information extracted by the intensity information extraction unit 27, and then widens a dynamic range by performing logarithmic transformation on the envelope.

The photoacoustic image construction unit 29 inputs the phase information from the phase information extraction unit 26, and inputs the intensity information after the detection and logarithmic transformation process from the detection and logarithmic transformation unit 28. The photoacoustic image construction unit 29 generates a photoacoustic image which is a distribution image of a light absorber, on the basis of the input phase information and intensity information. For example, the photoacoustic image construction unit 29 determines luminance (gradation value) of each pixel in the distribution image of the light absorber, on the basis of the input intensity information. In addition, for example, the photoacoustic image construction unit 29 determines color of each pixel (display color) in the distribution image of the light absorber, on the basis of the phase information. The photoacoustic image construction unit 29 determines color of each pixel on the basis of the input phase information, for example, using the range of phases 0° to 90° in a color map associated with a predetermined color.

Here, since the range of phases 0° to 45° is a range in which the first photoacoustic data is larger than the second photoacoustic data, a generation source of a photoacoustic signal is considered to be a vein through which blood flows, the blood mainly containing deoxygenated hemoglobin in which the amount of absorption of a wavelength of 756 nm is greater than that of a wavelength of 798 nm. On the other hand, since the range of phases 45° to 90° is a range in which the second photoacoustic data is smaller than the first photoacoustic data, the generation source of the photoacoustic signal is considered to be an artery through which blood flows, the blood mainly containing oxygenated hemoglobin in which the amount of absorption of a wavelength of 756 nm is less than that of a wavelength of 798 nm.

Consequently, as the color map, a color map is used in which color gradually changes so as to become blue at the phase of 0° and to become white as the phase approaches 45° and in which color gradually changes so as to become red at the phase of 90° and to become white as the phase approaches 45°. In this case, in the photoacoustic image, a portion corresponding to the artery can be expressed by red, and a portion corresponding to the vein can be expressed by blue. Color coding between the portion corresponding to the artery and the portion corresponding to the vein has only to be performed on the basis of the phase information, without using the intensity information. The image display unit 14 displays the photoacoustic image generated by the photoacoustic image construction unit 29 on a display screen.

Subsequently, a configuration of the laser light source unit 13 will be described in detail. FIG. 2 illustrates a configuration of the laser light source unit 13. The laser light source unit 13 includes a laser rod 51, a flash lamp 52, mirrors 53 and 54, a Q switch 55, a birefringent filter (BRF) 56, driving unit 57, rotational displacement detection unit 58, and a control unit 59. The laser rod 51 is a laser medium. For example, alexandrite crystal, Cr:LiSAF (Cr:LiSrAlF6), Cr:LiCAF (Cr:LiCaAlF6) crystal, or Ti:Sapphire crystal can be used as the laser rod 51. The flash lamp 52 is an excitation light source, and irradiates the laser rod 51 with excitation light. Any of light sources other than the flash lamp 52, for example, a semiconductor laser or a solid laser, may be used as the excitation light source.

The mirrors 53 and 54 face each other with the laser rod 51 interposed therebetween, and an optical resonator is constituted by the mirrors 53 and 54. The mirror 54 is assumed to be the output side. The Q switch 55 and the birefringent filter 56 are inserted into the optical resonator. An insertion loss within the optical resonator rapidly changes from a high loss (low Q) to a low loss (high Q) by the Q switch 55, and thus a pulse laser beam can be obtained. The birefringent filter 56 changes a transmission wavelength in association with rotational displacement and changes an oscillation wavelength of the optical resonator. The driving unit 57 rotates the birefringent filter 56. The rotational displacement detection unit 58 detects the rotational displacement of the birefringent filter 56.

The control unit 59 includes a rotation control unit 60 and an emission control unit 61. The rotation control unit 60 continuously rotates the birefringent filter at a predetermined rotation speed depending on the number of wavelengths included in a wavelength sequence of a pulse laser beam to be emitted. A rotation speed of the birefringent filter can be determined, for example, on the basis of change characteristics of an oscillation wavelength for the rotational displacement position in the birefringent filter 56, the number of wavelengths included in the wavelength sequence, and the number of times of emission of the pulse laser beam per unit time (interval of time between pulse laser beams).

The emission control unit 61 outputs a flash lamp trigger signal to the flash lamp 52, and irradiates the laser rod 51 with excitation light from the flash lamp 52. After the irradiation with the excitation light, the emission control unit 61 outputs a Q switch trigger signal to the Q switch 55 at a timing when the rotational displacement position of the birefringent filter 56 is set to a position corresponding to a wavelength of a pulse laser beam to be emitted. In addition, the emission control unit 61 outputs a Q switch synchronization signal to the ultrasonic wave unit 12 in accordance with an output timing of the Q switch trigger signal. The Q switch 55 rapidly changes the insertion loss within the optical resonator from a high loss to a low loss (Q switch is turned on) in response to the Q switch trigger signal, and thus the pulse laser beam is emitted from the mirror 54 on the output side.

Referring back to FIG. 1, the control unit 31 controls each unit within the ultrasonic wave unit 12. The trigger control circuit 30 outputs a BRF control signal for controlling the rotation of the birefringent filter 56 (FIG. 2) to the laser light source unit 13. In addition, the trigger control circuit 30 outputs a flash lamp standby signal for controlling the emission of the flash lamp 52 to the laser light source unit 13. For example, the trigger control circuit 30 receives the current rotational displacement position of the birefringent filter 56 from the rotation control unit 60 of the laser light source unit 13, and outputs the flash lamp standby signal at a timing based on the received rotational displacement position.

The trigger control circuit 30 inputs a Q switch synchronization signal indicating a timing at which the Q switch is turned on, that is, a laser emission timing, from the laser light source unit 13. When the trigger control circuit 30 receives the Q switch synchronization signal, the trigger control circuit outputs a sampling trigger signal (AD trigger signal) to the AD conversion unit 22. The AD conversion unit 22 starts to sample a photoacoustic signal on the basis of the sampling trigger signal.

Figure 3:
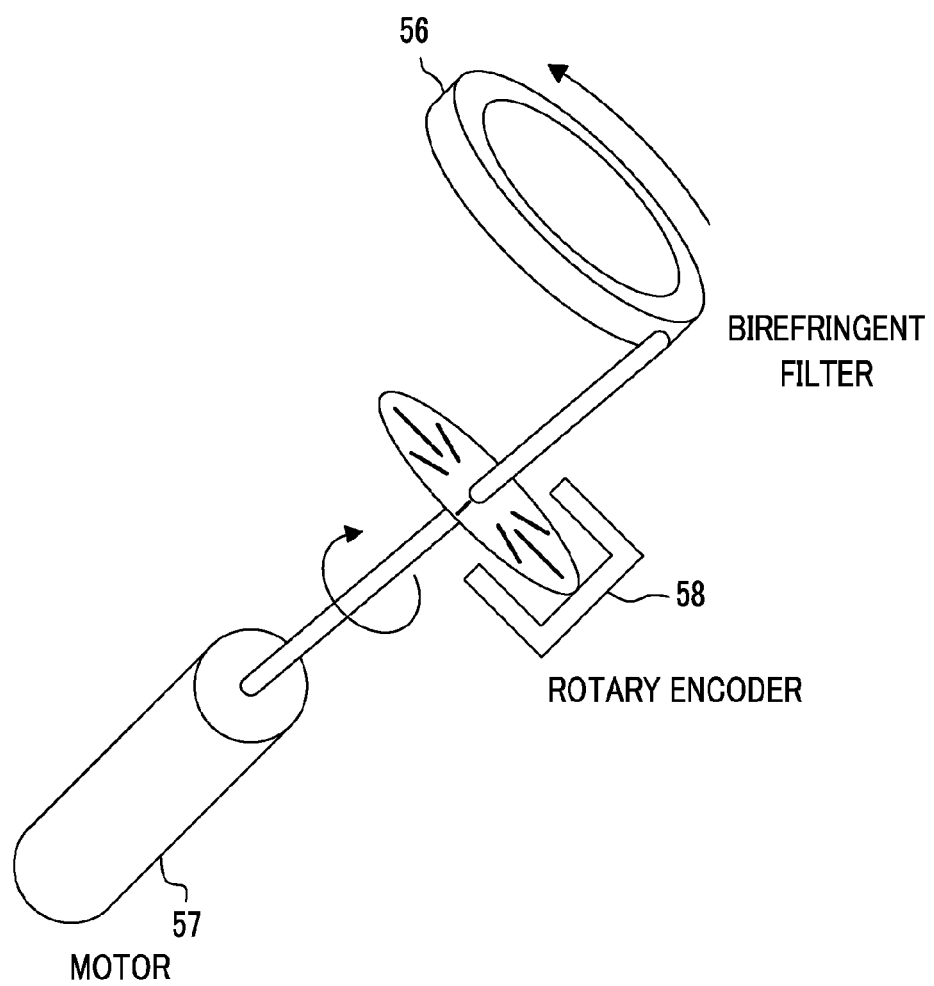
FIG. 3 is a perspective view illustrating a configuration example of a birefringent filter, driving unit, and rotational displacement detection unit.

FIG. 3 illustrates a configuration example of the birefringent filter 56, the driving unit 57, and the rotational displacement detection unit 58. In this example, the driving unit 57 is a servo motor, and the rotational displacement detection unit 58 is a rotary encoder. The birefringent filter 56 rotates in association with the rotation of an output axis of the servo motor. The rotary encoder detects the rotational displacement of the birefringent filter 56 by a rotating plate with a slit which is mounted to the output axis of the servo motor and a transmission-type photointerrupter. For example, the rotation control unit 60 (FIG. 2) controls a voltage or the like to be supplied to the servo motor so that the amount of rotational displacement of the rotation axis of the servo motor, which is detected by the rotary encoder for a predetermined period of time is maintained at a predetermined amount, thereby rotating the birefringent filter 56 at a predetermined speed.

Figure 4:
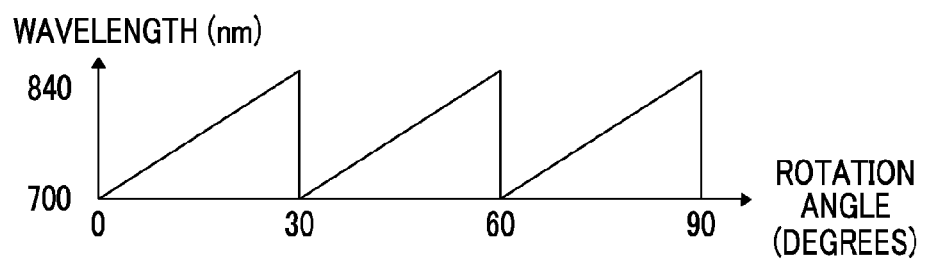
FIG. 4 is a graph illustrating an example of wavelength transmission characteristics for rotational displacement of the birefringent filter.

FIG. 4 illustrates an example of wavelength transmission characteristics (oscillation wavelength characteristics) with respect to the rotational displacement of the birefringent filter 56. The birefringent filter 56 changes an oscillation wavelength of an optical resonator, for example, between 700 nm and 840 nm. For example, the birefringent filter 56 repeats a free spectral range (FSR) three times between the rotational displacement positions of 0° and 90° (in ¼ rotation), and repeats the FSR twelve times for each rotation.

Figure 5:
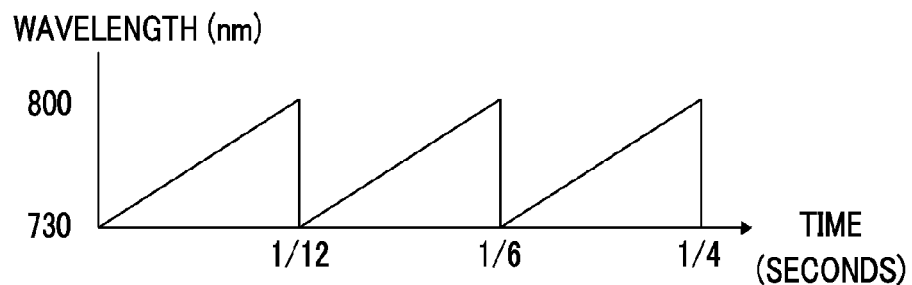
FIG. 5 is a graph illustrating oscillation wavelength characteristics when the birefringent filter is rotated at a speed of one rotation per second.

FIG. 5 illustrates oscillation wavelength characteristics when the above-mentioned birefringent filter 56 is rotated at a speed of one rotation per second. When the birefringent filter 56 which has wavelength transmission characteristics illustrated in FIG. 4 is rotated at a speed of one rotation per one second, the birefringent filter 56 repeats the FSR three times in ¼ seconds, and repeats the FSR twelve times (12 Hz) per second. As the rotation speed of the birefringent filter 56 increases, the number of times of repetition of the FSR per second is increased, and as the rotation speed thereof decreases, the number of times of repetition of the FSR per second is decreased.

Figure 6:
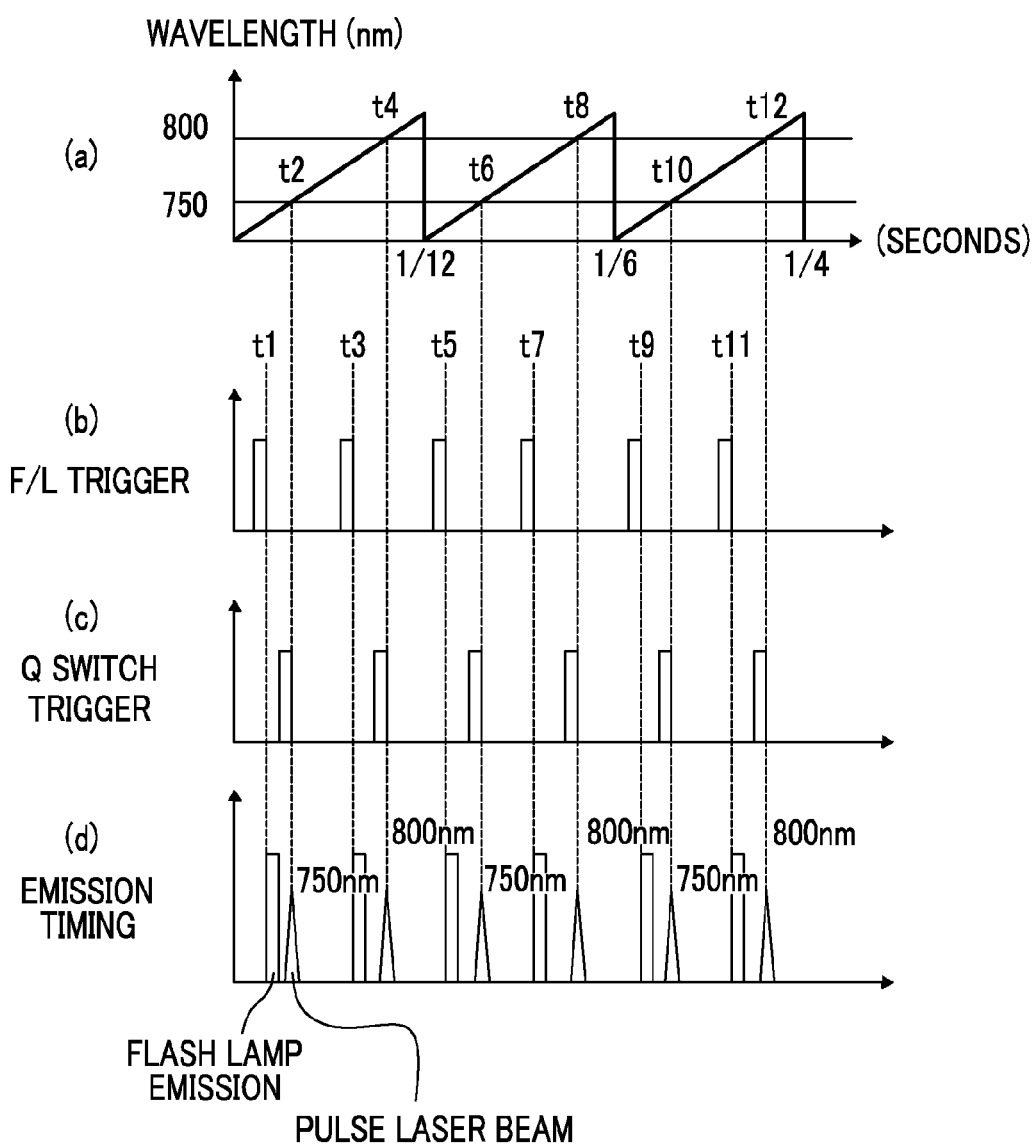
FIG. 6 is a timing chart illustrating various types of triggers and an emission timing.

FIG. 6 is a timing chart illustrating various types of triggers and an emission timing. (a) of FIG. 6 illustrates oscillation wavelength characteristics (transmission wavelength characteristics of the birefringent filter 56) of an optical resonator with respect to a time change. (b) of FIG. 6 illustrates a flash lamp trigger, and (c) of FIG. 6 illustrates a Q switch trigger. (d) of FIG. 6 illustrates an emission timing of a flash lamp and an emission timing of a pulse laser beam. Meanwhile, in FIG. 5, for the purpose of simplifying the description, a description is given on the assumption that the flash lamp 52 and the Q switch 55 instantaneously respond to a trigger, but actually a delay time is present. However, since the delay is approximately several μ seconds to 100μ seconds, the delay is negligible.

First, the trigger control circuit 30 of the ultrasonic wave unit 12 outputs the flash lamp standby signal in order to cause a pulse laser beam having a wavelength of 750 nm to be emitted from the laser light source unit 13. When the emission control unit 61 of the laser light source unit 13 receives the flash lamp standby signal, the emission control unit outputs the flash lamp trigger signal to the flash lamp 52 at time t1 ((b) of FIG. 6), and turns on the flash lamp 52 ((d) of FIG. 6). Thereafter, the emission control unit 61 outputs the Q switch trigger signal at time t2 when the rotational displacement position of the birefringent filter 56 is set to a position corresponding to the wavelength of 750 nm ((c) of FIG. 6), and turns on the Q switch 55 to cause the pulse laser beam having a wavelength of 750 nm to be emitted from the optical resonator.

Subsequently, the trigger control circuit 30 of the ultrasonic wave unit 12 outputs the flash lamp standby signal in order to cause a pulse laser beam having a wavelength of 800 nm to be emitted from the laser light source unit 13. When the emission control unit 61 receives the flash lamp standby signal, the emission control unit outputs the flash lamp trigger signal to the flash lamp 52 at time t3 ((b) of FIG. 6), and turns on the flash lamp 52 ((d) of FIG. 6). Thereafter, the emission control unit 60 outputs the Q switch trigger signal at time t4 when the rotational displacement position of the birefringent filter 56 is set to a position corresponding to the wavelength of 800 nm ((c) of FIG. 6), and turns on the Q switch 55 to cause the pulse laser beam having a wavelength of 800 nm to be emitted from the optical resonator.

Hereinafter, similarly, the emission control unit 61 outputs the flash lamp trigger signal to the flash lamp 52 at time t5, time t7, time t9, and time t11. In addition, the trigger control circuit outputs the Q switch trigger signal to the Q switch 55 at time t6, time t8, time t10, and time t12, and causes the pulse laser beam having a wavelength depending on the transmission wavelength of the birefringent filter 56 at each time to be emitted. The transmission wavelengths of the birefringent filter 56 at time t6 and time t10 are 750 nm, and the transmission wavelengths of the birefringent filter at time t8 and time t12 are 800 nm, and thus the laser light source unit 13 sequentially and repeatedly emits the pulse laser beams having wavelengths of 750 nm and 800 nm in this order.

In the example of FIG. 6, the laser light source unit 13 alternately emits two pulse laser beams of a pulse laser beam having a wavelength of 750 nm and a pulse laser beam having a wavelength of 800 nm in $1/12$ seconds. The laser light source unit 13 emits the pulse laser beam twenty-four times per second while switching the two wavelengths (24 Hz operation). In other words, the pulse laser beam having a set of two wavelengths is emitted in units of twelve sets per second.

Figure 7:
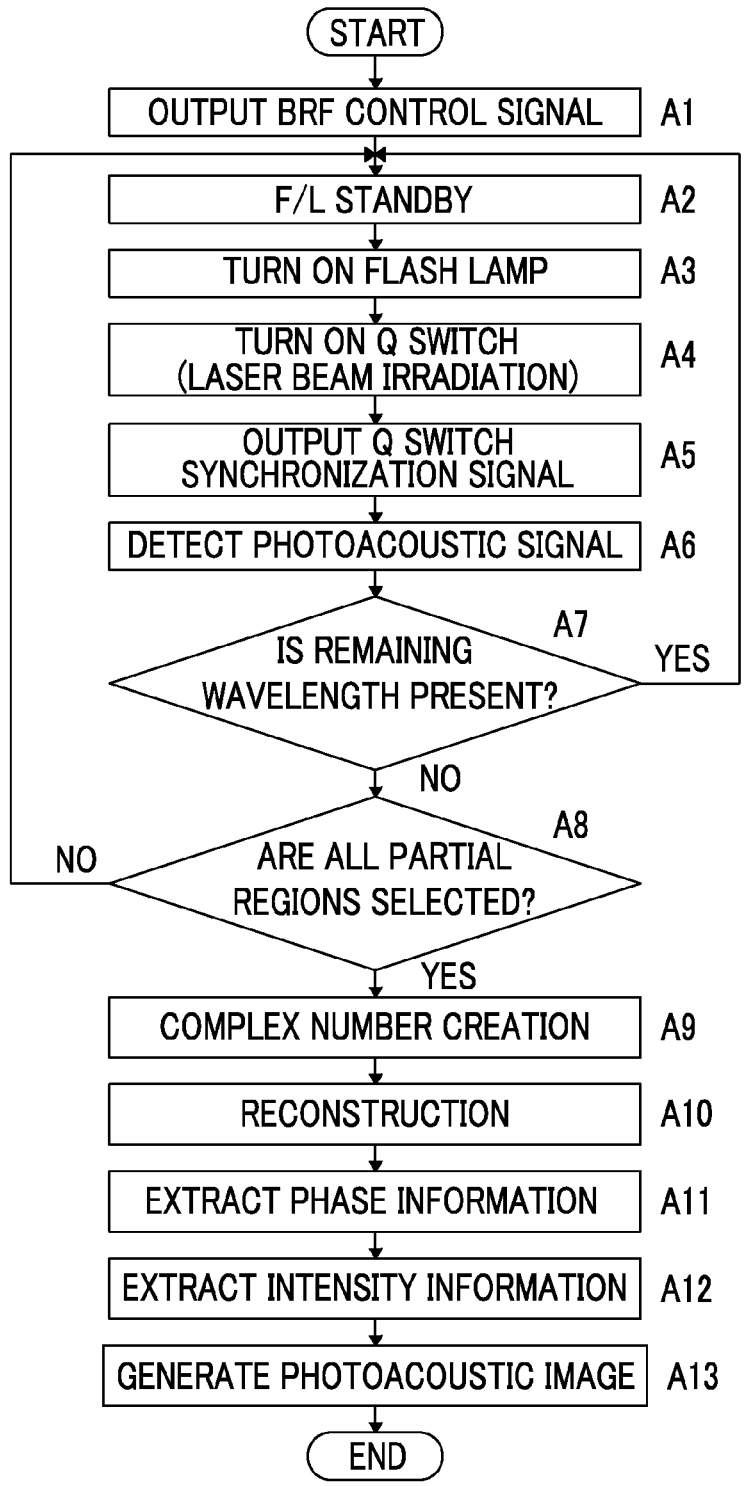
FIG. 7 is a flow chart illustrating an operation procedure of the photoacoustic image generation apparatus according to the first embodiment.

FIG. 7 illustrates an operation procedure of the photoacoustic image generation apparatus 10. Herein, a description will be given on the assumption that a region of a test object which is irradiated with a laser beam is divided into a plurality of partial regions. The trigger control circuit 30 of the ultrasonic wave unit 12 outputs the BRF control signal for rotating the birefringent filter 56 within the laser light source unit 13 at a predetermined rotation speed to the laser light source unit 13, prior to the irradiation with the pulse laser beam with respect to the test object (step A1). For example, when the birefringent filter 56 repeats an FSR twelve times during one rotation and the pulse laser beam having a wavelength of 750 nm and the pulse laser beam having a wavelength of 800 nm are sequentially emitted in $1/12$ seconds (in the case of 24 Hz operation), the trigger control circuit 30 outputs the BRF control signal for rotating the birefringent filter 56 once per second.

When the photoacoustic signal is ready to be received, the trigger control circuit 30 outputs the flash lamp trigger signal to the laser light source unit 13 at a predetermined timing in order to cause the pulse laser beam having a first wavelength (750 nm) constituting a wavelength sequence to be emitted (step A2). When the flash lamp standby signal is input, the emission control unit 61 of the laser light source unit 13 turns on the flash lamp 52 to cause the laser rod 51 to start to be excited (step A3). The emission control unit 61 turns on the flash lamp 52, for example, at a timing calculated back from a timing at which the rotational displacement position of the birefringent filter 56 is set to the position corresponding to the wavelength of 750 nm.

After the flash lamp 52 is turned on, the emission control unit 61 turns on the Q switch 55 at a timing when the rotational displacement position of the birefringent filter 56 is set to the position corresponding to the first wavelength (750 nm) constituting the wavelength sequence (step A4). The laser light source unit 13 emits the pulse laser beam having a wavelength of 750 nm by the Q switch 55 being turned on. The emission control unit 61 outputs the Q switch synchronization signal to the ultrasonic wave unit 12 in synchronization with the timing at which the Q switch 55 is turned on (step A5).

The pulse laser beam having a wavelength of 750 nm which is emitted from the laser light source unit 13 is guided to, for example, the probe 11, and a first partial region of the test object is irradiated with the pulse laser beam from the probe 11. A light absorber absorbs energy of the irradiated pulse laser beam within the test object, and thus a photoacoustic signal is generated. The probe 11 detects the photoacoustic signal generated within the test object. The photoacoustic signal detected by the probe 11 is received by the reception circuit 21.

After the flash lamp trigger signal is output, the trigger control circuit 30 stands by until the trigger control circuit receives the Q switch synchronization signal. When the trigger control circuit 30 receives the Q switch synchronization signal, the trigger control circuit outputs the sampling trigger signal to the AD conversion unit 22. The AD conversion unit 22 samples the photoacoustic signal received by the reception circuit 21 with a predetermined sampling period (step A6). The photoacoustic signal sampled by the AD conversion unit 22 is stored as first photoacoustic data in the reception memory 23.

The control unit 31 determines whether a remaining wavelength is present, in other words, whether the pulse laser beams having all the wavelengths constituting the wavelength sequence have been emitted (step A7). When a remaining wavelength is present, the process returns to step A2 in order to emit the pulse laser beam having the next wavelength, and the flash lamp standby signal is output to the laser light source unit 13 from the trigger control circuit 30. In step A3, the emission control unit 61 turns on the flash lamp 52, and in step A4, the emission control unit turns on the Q switch 55 at a timing when the birefringent filter 56 is set to be at the rotational displacement position corresponding to the second wavelength (800 nm) constituting the wavelength sequence, to cause the pulse laser beam to be emitted.

The pulse laser beam having a wavelength of 800 nm which is emitted from the laser light source unit 13 is guided to, for example, the probe 11, and the first partial region of the test object is irradiated with the pulse laser beam from the probe 11. The probe 11 detects a photoacoustic signal generated by the light absorber within the test object absorbing the pulse laser beam having a wavelength of 800 nm. When the trigger control circuit 30 receives the Q switch synchronization signal, the trigger control circuit outputs the sampling trigger signal to the AD conversion unit 22, and the AD conversion unit 22 samples the photoacoustic signal in step A6. The photoacoustic signal sampled by the AD conversion unit 22 is stored as second photoacoustic data in the reception memory 23. The photoacoustic image generation apparatus 10 performs step A1 to step A6 on the wavelengths constituting the wavelength sequence and irradiates the test object with the pulse laser beams having the wavelengths constituting the wavelength sequence, thereby detecting the photoacoustic signal from the test object.

When the control unit 31 determines in step A7 that a remaining wavelength is not present, the control unit determines whether all the partial regions have been selected (step A8). When a partial region to be selected remains, the process returns to step A2. The photoacoustic image generation apparatus 10 performs step A2 to step A7 on each partial region, sequentially irradiates each partial region with pulse laser beams having the wavelengths (750 nm and 800 nm) constituting the wavelength sequence, and stores the first photoacoustic data and the second photoacoustic data which correspond to each partial region, in the reception memory 23. When the irradiation with the pulse laser beam and the detection of the photoacoustic signal have been performed on all the partial regions, photoacoustic data required to generate a photoacoustic image of one frame is gathered.

When the control unit 31 determines in step A8 that all the partial regions have been selected, the process proceeds to the generation of the photoacoustic image. The complex number creation unit 24 reads out the first photoacoustic data and the second photoacoustic data from the reception memory 23, and generates complex number data in which first photoacoustic image data is set to a real part and second photoacoustic image data is set to an imaginary part (step A9). The photoacoustic image reconstruction unit 25 performs image reconstruction from the complex number data generated in step A9, using a Fourier transform method (FTA method) (step A10).

The phase information extraction unit 26 extracts phase information from the reconstructed complex number data (reconstructed image) (step A11). For example, when the reconstructed complex number data is expressed by X+iY, the phase information extraction unit 26 extracts the relation of $\theta=\tan^{-1}(Y/X)$ as the phase information (but, when the relation of X=0 is satisfied, the relation of $\theta=90°$ is satisfied). The intensity information extraction unit 27 extracts intensity information from the reconstructed complex number data (step A12). For example, when the reconstructed complex number data is expressed by X+iY, the intensity information extraction unit 27 extracts $(X^2+Y^2)^{1/2}$ as the intensity information.

The detection and logarithmic transformation unit 28 performs a detection and logarithmic transformation process on the intensity information extracted in step A12. The photoacoustic image construction unit 29 generates a photoacoustic image on the basis of the phase information extracted in step A11 and the performing of the detection and logarithmic transformation process, on the intensity information extracted in step A12 (step A13). For example, the photoacoustic image construction unit 29 generates the photoacoustic image by determining luminance (gradation value) of each pixel in a distribution image of a light absorber on the basis of the intensity information and by determining color of each pixel on the basis of the phase information. The generated photoacoustic image is displayed on the image display unit 14.

Figure 8:
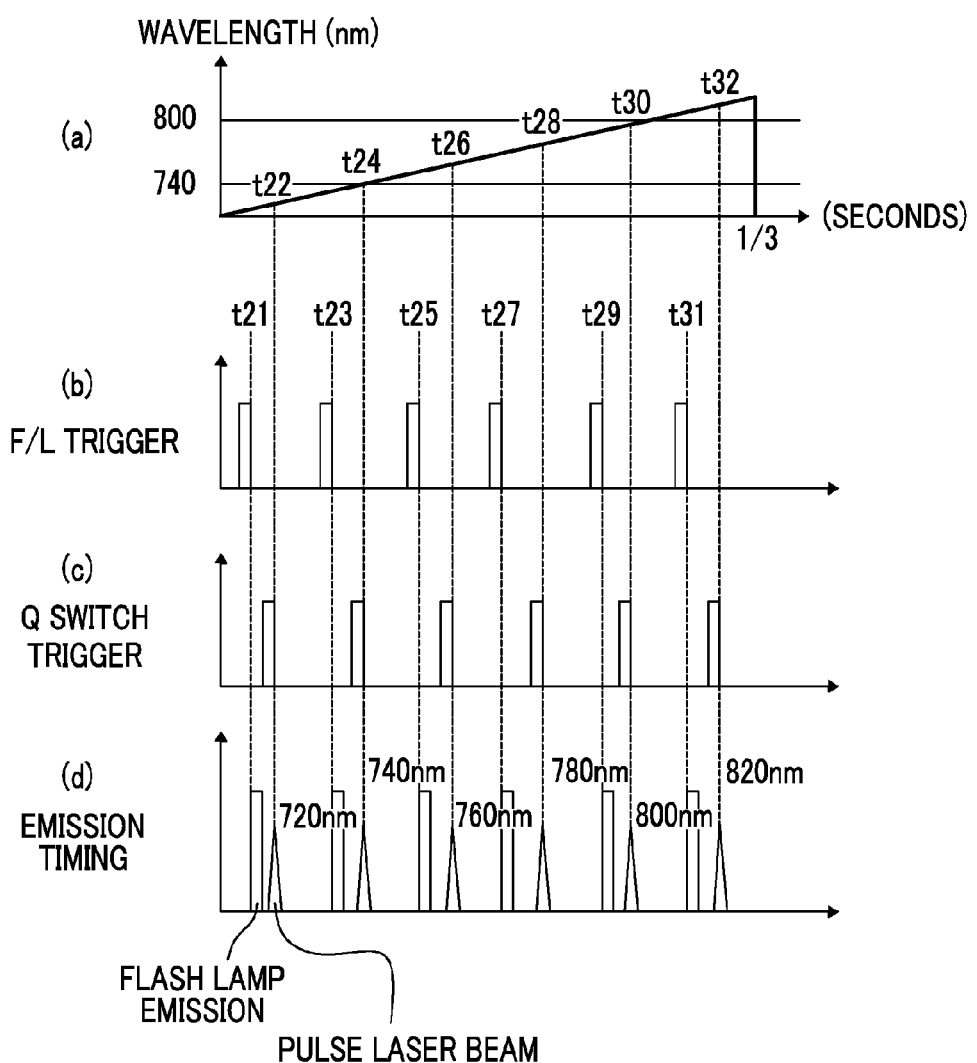
FIG. 8 is a timing chart illustrating various types of triggers and an emission timing in a case where a wavelength sequence includes six wavelengths.

Here, the rotation speed of the birefringent filter 56 may be appropriately determined depending on the number of wavelengths included in a wavelength sequence of a pulse laser beam to be emitted. Hereinafter, a case where the wavelength sequence includes six wavelengths (720 nm, 740 nm, 760 nm, 780 nm, 800 nm, and 820 nm) will be described. FIG. 8 is a timing chart illustrating various types of triggers and an emission timing when a wavelength sequence includes six wavelengths. (a) of FIG. 8 illustrates oscillation wavelength characteristics (transmission wavelength characteristics of the birefringent filter 56) of an optical resonator with respect to a time change. (b) of FIG. 8 illustrates a flash lamp trigger, and (c) of FIG. 8 illustrates a Q switch trigger. (d) of FIG. 8 illustrates an emission timing of a flash lamp and an emission timing of a pulse laser beam.

As illustrated in FIG. 4, when the birefringent filter 56 repeating an FSR twelve times in one rotation is rotated once in four seconds, the birefringent filter 56 is rotated ¼ per second and repeats the FSR three times per second ((a) of FIG. 8). First, the trigger control circuit 30 outputs the flash lamp standby signal in order to cause the pulse laser beam having a wavelength of 720 nm to be emitted from the laser light source unit 13. When the emission control unit 61 receives the flash lamp standby signal, the emission control unit outputs the flash lamp trigger signal to the flash lamp 52 at time t21 ((b) of FIG. 8), and turns on the flash lamp 52 ((d) of FIG. 8). Thereafter, the emission control unit 61 outputs the Q switch trigger signal at time t22 when the rotational displacement position of the birefringent filter 56 is set to the position corresponding to the wavelength of 720 nm ((c) of FIG. 8), and causes the pulse laser beam having a wavelength of 720 nm to be emitted from the optical resonator by the Q switch 55 being turned on.

Subsequently, the trigger control circuit 30 outputs the flash lamp standby signal in order to cause a pulse laser beam having a wavelength of 740 nm to be emitted from the laser light source unit 13. When the emission control unit 61 receives the flash lamp standby signal, the emission control unit outputs the flash lamp trigger signal to the flash lamp 52 at time t23 ((b) of FIG. 8), and turns on the flash lamp 52 ((d) of FIG. 8). Thereafter, the emission control unit 61 outputs the Q switch trigger signal at time t24 when the rotational displacement position of the birefringent filter 56 is set to the position corresponding to the wavelength of 740 nm ((c) of FIG. 8), and turns on the Q switch 55, thereby causing the pulse laser beam having a wavelength of 740 nm to be emitted from the optical resonator.

Hereinafter, similarly, the emission control unit 61 outputs the flash lamp trigger signal to the flash lamp 52 at time t25, time t27, time t29, and time t31. In addition, the trigger control circuit outputs the Q switch trigger signal to the Q switch 55 at time t26, time t28, time t30, and time t32, and causes the pulse laser beam having a wavelength depending on the transmission wavelength of the birefringent filter 56 at each time to be emitted. The transmission wavelengths of the birefringent filter 56 at time t26, time t28, time t30, and time t32 are 760 nm, 780 nm, 800 nm, and 820 nm, respectively, and the laser light source unit 13 emits six pulse laser beams having a wavelength increasing by 20 nm in ⅓ seconds in a range between 720 nm and 820 nm.

In an example of FIG. 8, the laser light source unit 13 emits a pulse laser beam having six wavelengths of 720 nm to 820 nm in ⅓ seconds. The laser light source unit 13 emits the pulse laser beam eighteen times per second while switching the six wavelengths (18 Hz operation). In other words, the pulse laser beams having a set of six wavelengths is emitted in units of three sets per second.

It is preferable that the rotation speed of the birefringent filter 56 be set so that a pulse laser beam having wavelengths constituting a wavelength sequence can be emitted in one FSR. For example, when the number of times of the FSR repeated by the birefringent filter 56 during one rotation is set to k[times/rotation], the number of wavelengths included in the wavelength sequence is set to n[pieces], and the number of times of emission of the pulse laser beam per unit time is set to m[times/second], the rotation speed of the birefringent filter 56 can be set to a value determined by the relation of v=m/(k×n)[rotations/second]. In this case, m pulse lasers can be emitted per second while switching n wavelengths for each FSR (m Hz operation).

In this embodiment, the flash lamp 52 is turned on to excite the laser rod 51 while rotating the birefringent filter 56 at a predetermined rotation speed. After the excitation of the laser rod, the Q switch 55 is turned on at a timing when the rotational displacement position of the birefringent filter 56 is set to a position corresponding to a wavelength of a pulse laser beam to be emitted. As the rotation speed of the birefringent filter 56 decreases, for example, the number of oscillation wavelengths capable of being selected in one FSR of the birefringent filter 56 can be increased. On the other hand, when the number of wavelengths included in the wavelength sequence is two, the speed of the switching of the two wavelengths can be increased by increasing the rotation speed of the birefringent filter 56. In this manner, in this embodiment, it is possible to emit a pulse laser beam in a desired wavelength sequence from the laser light source unit 13 by controlling the rotation speed of the birefringent filter 56.

In this embodiment, complex number data is generated in which one of the first photoacoustic data and the second photoacoustic data which are obtained at two wavelengths is set to a real part and the other is set to an imaginary part, and a reconstructed image is generated from the complex number data using a Fourier transform method. In this case, it is possible to effectively perform the reconstruction as compared with a case where the first photoacoustic data and the second photoacoustic data are separately reconstructed. A pulse laser beam having a plurality of wavelengths is irradiated, and a photoacoustic signal (photoacoustic data) at the time of the irradiation with a pulse laser beam having each wavelength is used, and thus it is possible to perform functional imaging using optical absorption properties of the respective light absorbers being different from each other depending on wavelengths.

In addition, in this embodiment, for example, when a light irradiation region is divided into three partial regions, a first partial region is sequentially irradiated with a pulse laser beam having a first wavelength and a pulse laser beam having a second wavelength, and a second partial region is sequentially irradiated with the pulse laser beam having the first wavelength and the pulse laser beam having the second wavelength, and then a third partial region is sequentially irradiated with the pulse laser beam having the first wavelength and the pulse laser beam having the second wavelength. In this embodiment, any partial region is consecutively irradiated with the pulse laser beam having the first wavelength and the pulse laser beam having the second wavelength, and then the irradiation moves to the next partial region. In this case, it is possible to shorten the time from the irradiation with the pulse laser beam having the first wavelength to the irradiation with the second wavelength at the same position, as compared with a case where the three partial regions are irradiated with the pulse laser beam having the first wavelength and are then irradiated with the pulse laser beam having the second wavelength. It is possible to suppress mismatching between the first photoacoustic data and the second photoacoustic data by shortening the time between the irradiation with the pulse laser beam having the first wavelength and the irradiation with the pulse laser beam having the second wavelength.

Figure 9:
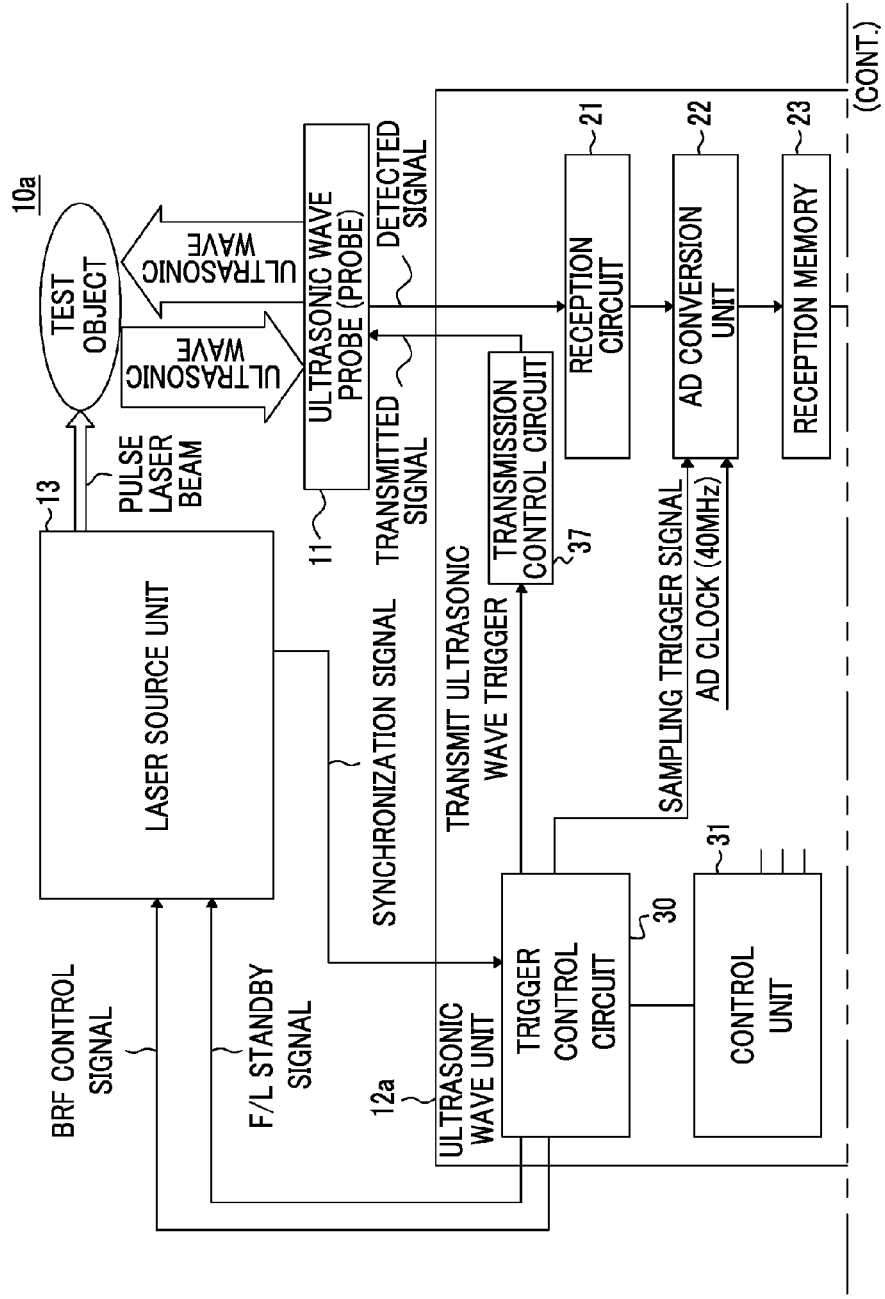
FIG. 9 is a block diagram illustrating a photoacoustic image generation apparatus according to a second embodiment of the invention.

Subsequently, a second embodiment of the invention will be described. FIG. 9 illustrates a photoacoustic image generation apparatus according to the second embodiment of the invention. In a photoacoustic image generation apparatus 10a according to this embodiment, an ultrasonic wave unit 12a includes data separation unit 32, ultrasonic image reconstruction unit 33, detection and logarithmic transformation unit 34, ultrasonic image construction unit 35, image synthesis unit 36, and a transmission control circuit 37, in addition to the configuration of the ultrasonic wave unit 12 in the photoacoustic image generation apparatus 10 according to the first embodiment which is illustrated in FIG. 1. The photoacoustic image generation apparatus 10 according to this embodiment is different from that in the first embodiment in that the apparatus generates an ultrasonic image in addition to a photoacoustic image. Other parts may be the same as those in the first embodiment.

In this embodiment, a probe 11 outputs (transmits) ultrasonic waves to a test object and detects (receives) reflected ultrasonic waves from the test object with respect to the transmitted ultrasonic waves, in addition to the detection of a photoacoustic signal. A trigger control circuit 30 transmits an ultrasonic wave transmission trigger signal for instructing the transmission of ultrasonic waves to the transmission control circuit 37 at the time of the generation of an ultrasonic image. When the transmission control circuit 37 receives the trigger signal, the transmission control circuit causes ultrasonic waves to be transmitted from the probe 11. The probe 11 detects reflected ultrasonic waves from the test object after the transmission of the ultrasonic waves.

The reflected ultrasonic waves detected by the probe 11 are input to AD conversion unit 22 through a reception circuit 21. The trigger control circuit 30 transmits a sampling trigger signal to the AD conversion unit 22 in accordance with the transmission timing of the ultrasonic waves, and starts to sample the reflected ultrasonic waves. The AD conversion unit 22 stores sampling data of the reflected ultrasonic waves (reflected ultrasonic data) in the reception memory 23.

The data separation unit 32 separates the reflected ultrasonic data stored in the reception memory 23 and first and second photoacoustic data from each other. The data separation unit 32 transmits the reflected ultrasonic data to the ultrasonic image reconstruction unit 33, and transmits the first and second photoacoustic data to complex number creation unit 24. The generation of the photoacoustic image on the basis of the first and second photoacoustic data is the same as that in the first embodiment. The data separation unit 32 inputs sampling data of the separated reflected ultrasonic waves to the ultrasonic image reconstruction unit 33.

The ultrasonic image reconstruction unit 33 generates pieces of data of lines of the ultrasonic image on the basis of reflected ultrasonic waves (sampling data thereof) which are detected by a plurality of ultrasonic vibrators of the probe 11. For example, the ultrasonic image reconstruction unit 33 adds data from 64 ultrasonic vibrators of the probe 11 on the basis of a delay time depending on the position of the ultrasonic vibrator to generate data for one line (delay addition method).

The detection and logarithmic transformation unit 34 obtains an envelope of the pieces of data of the lines which are output by the ultrasonic image reconstruction unit 33, and performs logarithmic transformation on the obtained envelope. The ultrasonic image construction unit 35 generates an ultrasonic image on the basis of the data of the lines on which the logarithmic transformation is performed. The ultrasonic image reconstruction unit 33, the detection and logarithmic transformation unit 34, and the ultrasonic image construction unit 35 constitute ultrasonic image generation unit that generates an ultrasonic image on the basis of reflected ultrasonic waves.

The image synthesis unit 36 synthesizes the photoacoustic image and the ultrasonic image. For example, the image synthesis unit 36 performs image synthesis by superimposing the photoacoustic image and the ultrasonic image on each other. At this time, it is preferable that the image synthesis unit 36 perform positioning so that corresponding points of the photoacoustic image and the ultrasonic image are set to be at the same position. The synthesized image is displayed on image display unit 14. It is also possible to display the photoacoustic image and the ultrasonic image on the image display unit 14 side by side without performing image synthesis, or to switch and display the photoacoustic image and the ultrasonic image.

Figure 10:
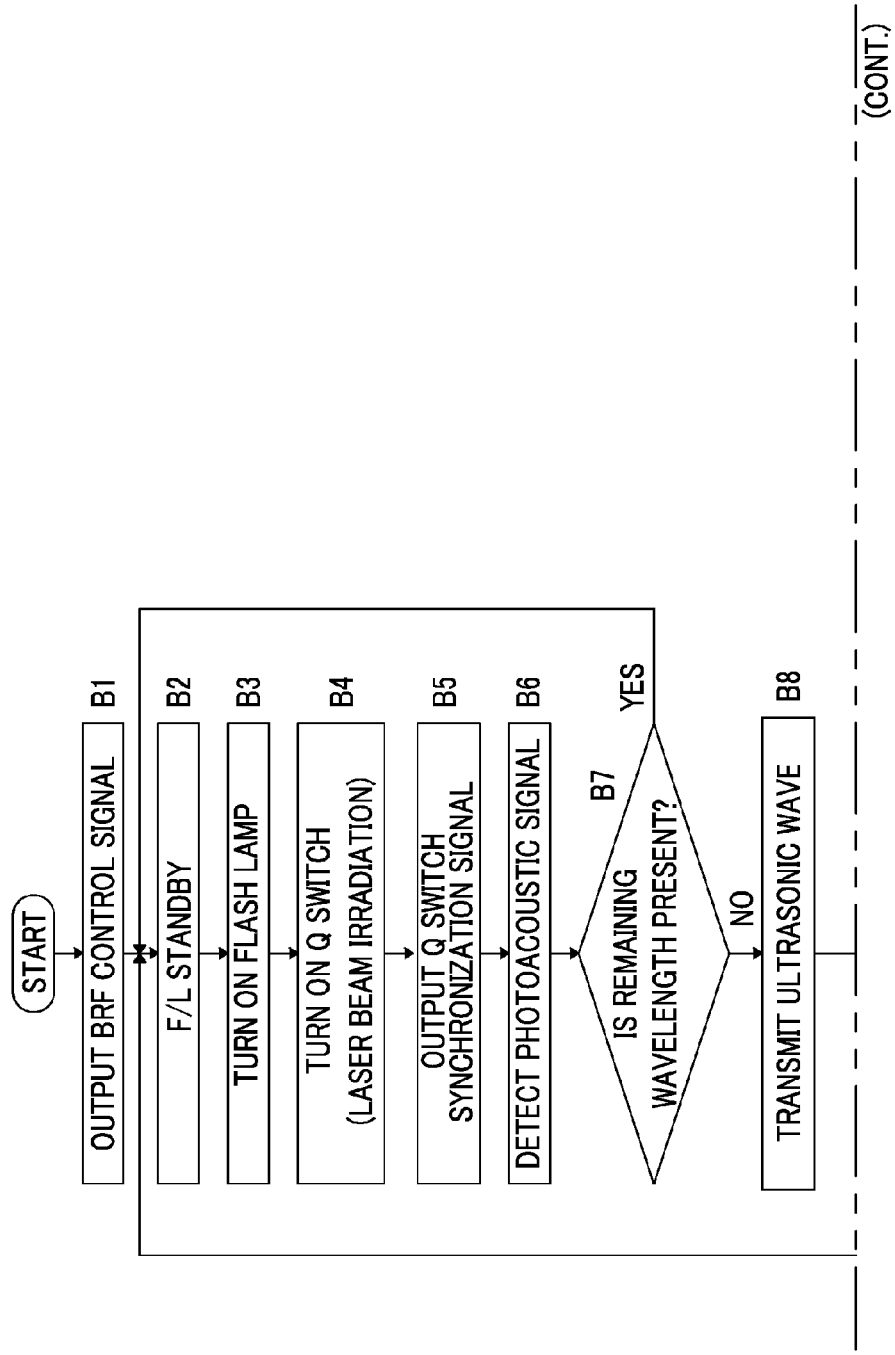
FIG. 10 is a block diagram illustrating an operation procedure of the photoacoustic image generation apparatus according to the second embodiment.

FIG. 10 illustrates an operation procedure of the photoacoustic image generation apparatus 10a Hereinafter, a description will be given on the assumption that a region of a test object which is irradiated with a laser beam is divided into a plurality of partial regions. The trigger control circuit 30 of the ultrasonic wave unit 12 outputs the BRF control signal for rotating birefringent filter 56 within a laser light source unit 13 at a predetermined rotation speed to the laser light source unit 13 (step B1).

When a photoacoustic signal is ready to be received, the trigger control circuit 30 outputs a flash lamp standby signal in order to cause a pulse laser beam having a first wavelength (750 nm) constituting a wavelength sequence to be emitted (step B2). When the flash lamp standby signal is input, an emission control unit 61 of the laser light source unit 13 turns on the flash lamp 52 to cause a laser rod 51 to start to be excited (step B3).

After the flash lamp 52 is turned on, the emission control unit 61 turns on the Q switch 55 at a timing when the rotational displacement position of the birefringent filter 56 is set to a position corresponding to the first wavelength (750 nm) constituting the wavelength sequence (step B4). The laser light source unit 13 emits a pulse laser beam having a wavelength of 750 nm by the Q switch 55 being turned on. The emission control unit 61 outputs the Q switch synchronization signal to the ultrasonic wave unit 12 in synchronization with a timing at which the Q switch 55 is turned on (step B5).

The pulse laser beam having a wavelength of 750 nm which is emitted from the laser light source unit 13 is guided to, for example, the probe 11, and a first region of the test object is irradiated with the pulse laser beam from the probe 11. A light absorber absorbs energy of the irradiated pulse laser beam within the test object, and thus a photoacoustic signal is generated. The probe 11 detects the photoacoustic signal generated within the test object. When the trigger control circuit 30 receives a Q switch synchronization signal, the trigger control circuit outputs a sampling trigger signal to the AD conversion unit 22. The AD conversion unit 22 receives the photoacoustic signal detected by the probe 11 through the reception circuit 21, and samples the photoacoustic signal with a predetermined sampling period (step B6). The photoacoustic signal sampled by the AD conversion unit 22 is stored as first photoacoustic data in the reception memory 23.

The control unit 31 determines whether a remaining wavelength is present, in other words, whether the pulse laser beams having all the wavelengths constituting the wavelength sequence have been emitted (step B7). When a remaining wavelength is present, the process returns to step B2 in order to cause the pulse laser beam having the next wavelength to be emitted, and the flash lamp standby signal is output to the laser light source unit 13 from the trigger control circuit 30. In step B3, the emission control unit 61 turns on the flash lamp 52, and in step B4, the emission control unit turns on the Q switch 55 at a timing when the birefringent filter 56 is set to be at the rotational displacement position corresponding to the second wavelength (800 nm) constituting the wavelength sequence, to cause the pulse laser beam to be emitted.

The pulse laser beam having a wavelength of 800 nm which is emitted from the laser light source unit 13 is guided to, for example, the probe 11, and the first partial region of the test object is irradiated with the pulse laser beam from the probe 11. The probe 11 detects the photoacoustic signal generated by the light absorber within the test object absorbing the pulse laser beam having a wavelength of 800 nm. When the trigger control circuit 30 receives the Q switch synchronization signal, the trigger control circuit outputs the sampling trigger signal to the AD conversion unit 22, and the AD conversion unit 22 samples the photoacoustic signal in step B6. The photoacoustic signal sampled by the AD conversion unit 22 is stored as second photoacoustic data in the reception memory 23. The photoacoustic image generation apparatus 10 performs step B1 to step B6 on the wavelengths constituting the wavelength sequence, and irradiates the test object with the pulse laser beams having the wavelengths constituting the wavelength sequence, thereby detecting the photoacoustic signal from the test object. The step B1 to step B6 may be the same as step A1 to step A6 of FIG. 7.

When the control unit 31 determines in step B7 that a remaining wavelength is not present, the process proceeds to the transmission and reception of ultrasonic waves. The trigger control circuit 30 transmits the ultrasonic waves to the test object from the probe 11 through the transmission control circuit 37 (step B8). In step B8, the ultrasonic waves are transmitted to the same region as the partial region of the test object which is irradiated with the pulse laser beam. The probe 11 detects reflected ultrasonic waves with respect to the transmitted ultrasonic waves (step B9). The detected reflected ultrasonic waves are sampled in the AD conversion unit 22 through the reception circuit 21, and are stored as reflected ultrasonic data in the reception memory 23.

The control unit 31 determines whether all the partial regions have been selected (step B10). When the partial region to be selected remains, the process returns to step B2. The photoacoustic image generation apparatus 10 performs step B2 to step B7 on each partial region, sequentially irradiates each partial region with pulse laser beams having the wavelengths (750 nm and 800 nm) constituting the wavelength sequence, and stores the first photoacoustic data and the second photoacoustic data in the reception memory 23. In addition, step B8 and step B9 are performed to store the reflected ultrasonic data in the reception memory 23. When the irradiation with the pulse laser beam, the detection of the photoacoustic signal, and the transmission and reception of the ultrasonic waves are performed on all the partial regions, data required to generate a photoacoustic image and an ultrasonic image of one frame is gathered.

When the control unit 31 determines in step B10 that all the partial regions have been selected, the process proceeds to the generation of the photoacoustic image and the ultrasonic image. The data separation unit 32 separates the first and second photoacoustic data and the reflected ultrasonic data from each other. The data separation unit 32 transmits the separated first and second photoacoustic data to the complex number creation unit 24, and transmits the reflected ultrasonic data to the ultrasonic image reconstruction unit 33. The complex number creation unit 24 generates complex number data in which first photoacoustic image data is set to a real part and second photoacoustic image data is set to an imaginary part (step B11). The photoacoustic image reconstruction unit 25 performs image reconstruction from the complex number data generated in step B11, using a Fourier transform method (FTA method) (step B12).

The phase information extraction unit 26 extracts phase information from the reconstructed complex number data (step B13). The intensity information extraction unit 27 extracts intensity information from the reconstructed complex number data (step B14). The detection and logarithmic transformation unit 28 performs a detection and logarithmic transformation process on the intensity information extracted in step B14. The photoacoustic image construction unit 29 generates a photoacoustic image on the basis of the phase information extracted in step B13 and the performing of the detection and logarithmic transformation process on the intensity information extracted in step B14 (step B15). Here, step B11 to step B15 may be the same as step A9 to step A13 of FIG. 7.

The ultrasonic image reconstruction unit 33 generates pieces of data of lines of the ultrasonic image using, for example, a delay addition method. The detection and logarithmic transformation unit 34 obtains an envelope of the pieces of data of the lines which are output by the ultrasonic image reconstruction unit 33, and performs logarithmic transformation on the obtained envelope. The ultrasonic image construction unit 35 generates an ultrasonic image on the basis of the pieces of data of the lines on which the logarithmic transformation is performed (step B16). The image synthesis unit 36 synthesizes the photoacoustic image and the ultrasonic image and displays the synthesized image on the image display unit 14 (step B17).

In this embodiment, the photoacoustic image generation apparatus generates an ultrasonic image in addition to a photoacoustic image. It is possible to observe a portion not capable of being formed as an image in the photoacoustic image by referring to the ultrasonic image. Other effects are the same as those in the first embodiment.

Meanwhile, in the above-described embodiments, an example in which first photoacoustic data and second photoacoustic data are created as complex numbers has been described, but the first photoacoustic data and the second photoacoustic data may be separately reconstructed without being created as complex numbers. Furthermore, herein, a ratio between the first photoacoustic data and the second photoacoustic data is calculated by the creation of complex numbers and by using phase information, but the same effect is obtained even though the ratio is calculated from intensity information of both the pieces of data. In addition, the intensity information can be generated on the basis of signal intensity in a first reconstructed image and signal intensity in a second reconstructed image.

In the generation of a photoacoustic image, the number of wavelengths of a pulse laser beam with which a test object is to be irradiated is not limited two, and the test object may be irradiated with three or more pulse laser beams, and thus the photoacoustic image may be generated on the basis of pieces of photoacoustic data corresponding to the respective wavelengths. In this case, for example, the phase information extraction unit 26 may generate a magnitude relation between relative signal intensities of the pieces of photoacoustic data corresponding to the respective wavelengths, as phase information. In addition, the intensity information extraction unit 27 may generate the signal intensities in the pieces of photoacoustic data corresponding to the respective wavelengths, which are grouped into one, as intensity information.

In FIG. 3, an example has been described in which a servo motor is used as the driving unit 57 and the birefringent filter 56 is rotated by rotating the servo motor, but any means rotating the birefringent filter 56 may be used as the driving unit 57 and is not limited to the servo motor. For example, a stepping motor can also be used as the driving unit 57. In this case, the rotation control unit 60 may control a pulse interval of a pulse signal which is supplied to the stepping motor so that the birefringent filter 56 is rotated at a predetermined rotation speed. When the stepping motor is used, the rotational displacement detection unit 58 may be omitted.

As described above, the invention has been described on the basis of the preferred embodiments, a laser light source unit, a control method thereof, a photoacoustic image generation apparatus, and a photoacoustic image generation method of the invention are not limited to those in the above-described embodiments, and various corrections and modifications made to the configurations of the above-described embodiments may also be included in the scope of the invention.

What is claimed is:

1. A laser source unit that sequentially emits a plurality of pulse laser beams in a predetermined wavelength sequence including at least two different wavelengths, the laser source unit comprising:
    a laser rod;
    an excitation light source that irradiates the laser rod with excitation light;
    an optical resonator including a pair of mirrors facing each other with the laser rod interposed therebetween;
    a Q switch which is inserted into the optical resonator;
    a birefringent filter which is inserted into the optical resonator and changes an oscillation wavelength of the optical resonator in association with rotational displacement of the birefringent filter;
    a rotation control unit that rotates the birefringent filter at a predetermined rotation speed depending on the number of wavelengths included in the wavelength sequence; and
    an emission control unit that irradiates the laser rod with excitation light from the excitation light source and then turns on the Q switch, at a timing when a rotational displacement angle of the birefringent filter is set to a position where the optical resonator oscillates at the wavelength of the pulse laser beam to be emitted, to cause the pulse laser beam to be emitted, wherein
    the rotation control unit sets the predetermined rotation speed of the birefringent filter, wherein
    the laser source unit emits the pulse laser beam in one free spectral range based on the predetermined rotation speed set by the rotation control unit,
    the predetermined rotation speed is determined on the basis of changes in an oscillation wavelength for the rotational displacement angle of the birefringent filter, the number of wavelengths included in the wavelength sequence, and the number of times of emission of the pulse laser beam per unit time, and
    the free spectral range is repeated a number of times during a single rotation.

2. The laser source unit according to claim 1, wherein when the number of times that the free spectral range is repeated during one rotation is set to k{times/rotation}, the number of wavelengths included in the wavelength sequence is set to n{pieces}, and the number of times of emission of the pulse laser beam per unit time is set to ni{times/second}, the predetermined rotation speed of the birefringent filter is determined as a value calculated by a relation of v=m/(k×n){rotations/second}.

3. The laser source unit according to claim 2, wherein the rotation control unit continuously sends a signal for rotating the birefringent filter in a predetermined direction at the predetermined rotation speed.

4. The laser source unit according to claim 2, further comprising:
a servo motor that rotates the birefringent filter; and
a rotary encoder that detects the rotational displacement of the birefringent filter,
wherein the rotation control unit controls the servo motor so that the amount of rotational displacement of the birefringent filter detected by the rotary encoder for a predetermined period of time is set to an amount depending on the predetermined rotation speed.

5. The laser source unit according to claim 1, wherein the rotation control unit continuously sends a signal for rotating the birefringent filter in a predetermined direction at the predetermined rotation speed.

6. The laser source unit according to claim 1, further comprising:
a servo motor that rotates the birefringent filter; and
a rotary encoder that detects the rotational displacement of the birefringent filter,
wherein the rotation control unit controls the servo motor so that the amount of rotational displacement of the birefringent filter detected by the rotary encoder for a predetermined period of time is set to an amount depending on the predetermined rotation speed.

7. The laser source unit according to claim 1, wherein the birefringent filter is rotated by a stepping motor, and the rotation control unit controls a pulse interval of a pulse signal supplied to the stepping motor so that the birefringent filter is rotated at the predetermined rotation speed.

8. A photoacoustic image generation apparatus comprising:
a laser source unit that sequentially emits a plurality of pulse laser beams in a predetermined wavelength sequence including at least two different wavelengths;
a detection unit that detects a photoacoustic signal generated within an object when the object is irradiated with the pulse laser beam having each wavelength included in the predetermined wavelength sequence, and generates pieces of photoacoustic data corresponding to the respective wavelengths;
an intensity ratio extraction unit that extracts a magnitude relation between relative signal intensities of the pieces of photoacoustic data corresponding to the respective wavelengths;
a photoacoustic image construction unit that generates a photoacoustic image on the basis of the extracted magnitude relation, wherein
the laser source unit includes
a laser rod,
an excitation light source that irradiates the laser rod with excitation light,
an optical resonator including a pair of mirrors facing each other with the laser rod interposed therebetween,
a Q switch which is inserted into the optical resonator,
a birefringent filter which is inserted into the optical resonator and changes an oscillation wavelength of the optical resonator in association with rotational displacement of the birefringent filter, a rotation control unit that rotates the birefringent filter at a predetermined rotation speed depending on the number of wavelengths included in the wavelength and sequence, and
an emission control unit that irradiates the laser rod with excitation light from the excitation light source and then turns on the Q switch, at a timing when a rotational displacement angle of the birefringent filter is set to a position where the optical resonator oscillates at the wavelength of the pulse laser beam to be emitted, to cause the pulse laser beam to be emitted, wherein
the rotation control unit sets the predetermined rotation speed of the birefringent filter,
the laser source unit emits the pulse laser beam in one free spectral range based on the predetermined rotation speed set by the rotation control unit,
the predetermined rotation speed is determined on the basis of changes in an oscillation wavelength for the rotational displacement angle of the birefringent filter, the number of wavelengths included in the wavelength sequence, and the number of times of emission of the pulse laser beam per unit time, and
the free spectral range is repeated a number of times during a single rotation.

9. The photoacoustic image generation apparatus according to claim 8, further comprising an intensity information extraction unit that generates intensity information indicating signal intensity on the basis of the pieces of photoacoustic data corresponding to the respective wavelengths,
wherein the photoacoustic image construction unit determines a gradation value of each pixel of the photoacoustic image on the basis of the intensity information, and determines a display color of each pixel on the basis of the extracted magnitude relation.

10. The photoacoustic image generation apparatus according to claim 9,
wherein the predetermined wavelength sequence includes a first wavelength and a second wavelength,
wherein the photoacoustic image generation apparatus further comprises:
a complex number creation unit that generates complex number data in which one of first photoacoustic data corresponding to a photoacoustic signal, detected when irradiation with the pulse laser beam having the first wavelength is performed, and second photoacoustic data corresponding to a photoacoustic signal, detected when irradiation with the pulse laser beam having the second wavelength is performed, is set to a real part and the other one is set to an imaginary part; and
a photoacoustic image reconstruction unit that generates a reconstructed image from the complex number data using a Fourier transform method, and
wherein the intensity ratio extraction unit extracts the magnitude relation from the reconstructed image, and the intensity information extraction unit extracts the intensity information from the reconstructed image.

11. The photoacoustic image generation apparatus according to claim 10,
wherein the detection unit further detects reflected acoustic waves with respect to acoustic waves transmitted to the object to generate reflected acoustic wave data, and
wherein the photoacoustic image generation apparatus further comprises an acoustic wave image generation unit that generates an acoustic wave image on the basis of the reflected acoustic wave data.

12. The photoacoustic image generation apparatus according to claim 9,
   wherein the detection unit further detects reflected acoustic waves with respect to acoustic waves transmitted to the object to generate reflected acoustic wave data, and
   wherein the photoacoustic image generation apparatus further comprises an acoustic wave image generation unit that generates an acoustic wave image on the basis of the reflected acoustic wave data.

13. The photoacoustic image generation apparatus according to claim 8,
   wherein the detection unit further detects reflected acoustic waves with respect to acoustic waves transmitted to the object to generate reflected acoustic wave data, and
   wherein the photoacoustic image generation apparatus further comprises an acoustic wave image generation unit that generates an acoustic wave image on the basis of the reflected acoustic wave data.

* * * * *